US012702834B2

(12) United States Patent
Widge

(10) Patent No.: US 12,702,834 B2
(45) Date of Patent: Aug. 11, 2026

(54) SYSTEMS AND METHODS FOR MEASURING AND ALTERING BRAIN ACTIVITY RELATED TO FLEXIBLE BEHAVIOR

(71) Applicant: REGENTS OF THE UNIVERSITY OF MINNESOTA, Minneapolis, MN (US)

(72) Inventor: Alik Widge, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 358 days.

(21) Appl. No.: 18/034,368

(22) PCT Filed: Oct. 28, 2021

(86) PCT No.: PCT/US2021/057109

§ 371 (c)(1),
(2) Date: Apr. 27, 2023

(87) PCT Pub. No.: WO2022/094123

PCT Pub. Date: May 5, 2022

(65) Prior Publication Data

US 2024/0017069 A1 Jan. 18, 2024

Related U.S. Application Data

(60) Provisional application No. 63/107,274, filed on Oct. 29, 2020.

(51) Int. Cl.

| | |
|---|---|
| *A61N 1/36* | (2006.01) |
| *A61B 5/16* | (2006.01) |
| *A61B 5/374* | (2021.01) |

(52) U.S. Cl.

CPC .......... *A61N 1/36082* (2013.01); *A61B 5/162* (2013.01); *A61B 5/374* (2021.01); *A61N 1/36139* (2013.01)

(58) Field of Classification Search

CPC ............ A61N 1/36082; A61N 1/36139; A61N 2/006; A61B 5/162; A61B 5/374; A61B 5/0042; A61B 5/165

See application file for complete search history.

(56) References Cited

U.S. PATENT DOCUMENTS

| | | | |
|---|---|---|---|
| 2004/0138578 | A1 | 7/2004 | Pineda et al. |
| 2012/0232410 | A1 | 9/2012 | Freer et al. |
| 2014/0088672 | A1 | 3/2014 | Bedenbaugh |
| 2018/0192936 | A1 | 7/2018 | Widge et al. |

OTHER PUBLICATIONS

International Searching Authority—US, International Search Report and Written Opinion, for corresponding International App. No. PCT/US2021/057109, mailed Jan. 28, 2022 [7 pgs.].

Basu, et al., Closed loop enhancement and neural decoding of human cognitive control, bioRiv preprint doi: https://doi.org/10.1101/2020.04.24.059964 [46 pgs.].

*Primary Examiner* — Mark W. Bockelman

(74) *Attorney, Agent, or Firm* — QUARLES & BRADY LLP

(57) ABSTRACT

A method for controlling flexible behavior by stimulating a plurality of brain regions of a subject that includes receiving signals from a source region of the subject's brain, determining at least one signal indicative of out-of-range behavioral inflexibility from the source region in a predetermined frequency band and delivering at least one stimulation pulse to at least one target region of the subject's brain based on the at least one signal.

22 Claims, 18 Drawing Sheets

SYSTEMS AND METHODS FOR MEASURING AND ALTERING BRAIN ACTIVITY RELATED TO FLEXIBLE BEHAVIOR

CROSS-REFERENCES TO RELATED APPLICATIONS

This application is a United States National Phase Application under U.S.C. § 371 of International Patent Application No. PCT/US2021/057109 filed Oct. 28, 2021, which in turn claims priority to U.S. Provisional Patent Application No. 63/107,274, filed on Oct. 29, 2020, the contents of both of which are incorporated by reference in their entireties for all purposes.

STATEMENT REGARDING FEDERALLY SPONSORED RESEARCH

Not Applicable.

BACKGROUND

Mental disorders are a leading source of medical economic burden. Current therapies do not target the cause of these disorders and try to detect/treat ill-specified constructs such as mood.

SUMMARY

In accordance with one aspect of the disclosure, systems and methods are provided for assessing or measuring behavioral flexibility and/or for adjusting or influencing such behavior by stimulating a plurality of brain regions of a subject. The system may include a signal detection module for receiving physiologic signals from at least one source region of the subject's brain, a signal generation module for generating at least one stimulation pulse, and a processor coupled to the signal detection module and signal generation module. The processor can be programmed to receive the physiologic signals from the at least one source region from the signal detection module, receive behavioral signals from the subject, determine at least one signal among the physiologic signals and the behavioral signals that is indicative of out-of-range behavioral flexibility, and control the signal generation module to generate at least one stimulation pulse based on the at least one signal indicative of the out-of-range behavioral flexibility and to deliver the at least one stimulation pulse to at least one target region.

In accordance with one aspect of the disclosure, systems and methods for stimulation control for treating behavioral or cognitive inflexibility of a subject is provided. The system can include a signal detection module for receiving signals from at least one source region of the subject's brain, a signal generation module for generating at least one stimulation pulse, and a processor coupled to the signal detection module and signal generation module. The processor can be programmed to estimate model parameters based on behavioral and physiologic data, implement a real-time engine that tracks a flexibility level of the subject using the model parameters as applied to the signals, determine if the flexibility level is outside of a predetermined threshold range, and, upon the determination that the flexibility level is outside of the predetermined threshold range, cause the signal generation module to deliver a stimulation to at least one target region of the subject's brain.

The foregoing and other advantages of the present disclosure will appear from the following description.

BRIEF DESCRIPTION OF THE DRAWINGS

The present invention will hereafter be described with reference to the accompanying drawings, wherein like reference numerals denote like elements.

DETAILED DESCRIPTION

Figure 1A:
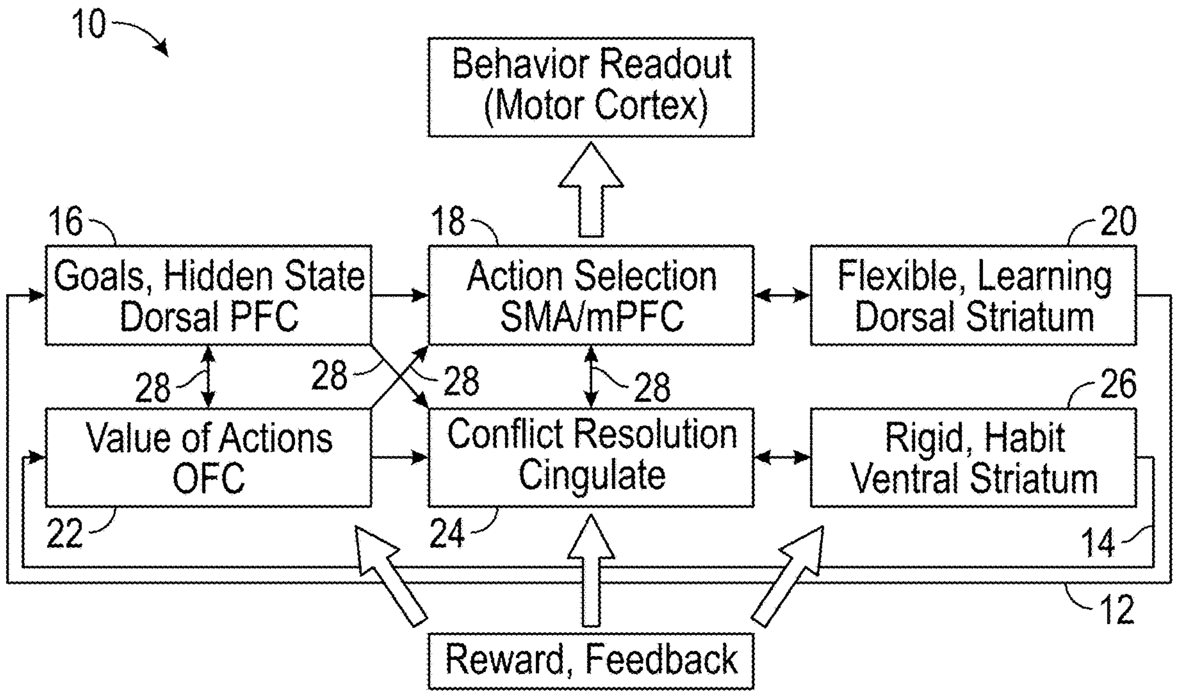
FIG. 1A is an exemplary illustration of cortico-striatal loop circuits.

The present disclosure relates generally to systems and methods for measuring and/or altering brain activity and more particularly to systems and methods for measuring and/or altering inflexible behavior.

Rigid, Repetitive, Inflexible Behavior and Cortico-Striatal Loops

Repetitive, rigid, inflexible behaviors (RRBs) are known to be a hallmark of a variety of disorders, including autism-spectrum disorders (ASDs), and other kinds of inflexibility disorders such as obsessive compulsive disorder (OCD), schizophrenia, and post-traumatic stress disorder (PTSD). RRBs can be particularly difficult to treat, in part, because their origin is unclear. Cognitively, RRBs can arise from problems in selecting the most adaptive response to a situation. That type of adaptive behavior is strongly linked to loop-like circuits connecting cortex, striatum, and thalamus. In some cases, these loops are implicated in tasks that can require flexible decision-making.

Cortico-striatal circuit abnormalities can be correlated with perseverative behavior in humans, and developmental changes in these circuits track the capacity for top-down control. Loops through lateral and ventral striatum may support habit-driven, less flexible behavior, while dorsal striatal loops can support flexibility. These two systems may compete, with medial prefrontal cortex (PFC), supplementary motor area (SMA), and cingulate acting as mediators. Further, cortico-striatal loops can be impaired in inflexibility disorder neuro-imaging studies. A key gap in the current state of the art, however, can be understanding the network physiology of these loops. Individual components' functions are partly known (e.g., value encoding in orbitofrontal cortex (OFC), higher-level goals in dorsal PFC, and flexibility in dorsal striatum), but the current state of the art lacks a clear model of how information flows between nodes or how that flow might break down in inflexibility disorders.

Local Field Potential as a Circuit Organizing Mechanism

Information transfer may involve inter-regional synchrony (coherence) of low-frequency local field potentials (LFP). Neurons can be more likely to fire when they receive input at the (depolarized) trough of an oscillation. Coherent oscillations can synchronize excitability, so that a spiking ensemble in one region more readily influences its counterpart in another region—if those ensembles are both locked to their local LFP. In the cortico-striatal loop, ensembles can communicate across regions through theta (e.g., 5-8 Hz) oscillations. PFC theta can be strongly associated with top-down control and flexibility. Some non-limiting examples may include attention steering in macaques, response suppression in rodents, and humans performing cognitive control tasks. This model can lead to the following: first, that both inter-regional theta coherence and local spike-theta coherence correlates with behavior; and second, that perseveration vs. flexibility depends on which PFC-striatal pathway is more coherent.

Therefore, given the above non-limiting examples, there is a need for improved systems and methods for monitoring, determining, and measuring behavioral inflexibility and systems and methods to adjust the inflexible behavior.

FIG. 1A is a non-limiting exemplary illustration of cortico-striatal loop circuits 10. Prefrontal regions are interconnected both with each other and with subdivisions of the striatum. These interconnections take the form of parallel loops 12, 14. The first loop can be a dorsal loop 12. The dorsal loop 12 may include the dorsal PFC 16, SMA 18, and dorsal striatum 20. The dorsal loop 12 can be subservient of more flexible and goal-directed behavior. The second loop can be a ventral loop 14. The ventral loop 14 may include the OFC 22, the cingulate 24, and the ventral striatum 26. The ventral loop 14 can be oriented more towards habitual, repetitive behavior. Further, the dorsal loop 12 and the ventral loop 14 can interconnect at multiple points, allowing them to influence each other. For example, synchrony links 28 can interconnect multiple regions of the brain, and specifically, connect the dorsal loop 12 and the ventral loop 14. In this framework, restrictive/repetitive behaviors can be represented as an over-function of ventral loops 24, a hypo-function of dorsal loops 12, or as an inability of prefrontal circuits to properly regulate the balance between the two parallel loops.

Figure 1B:
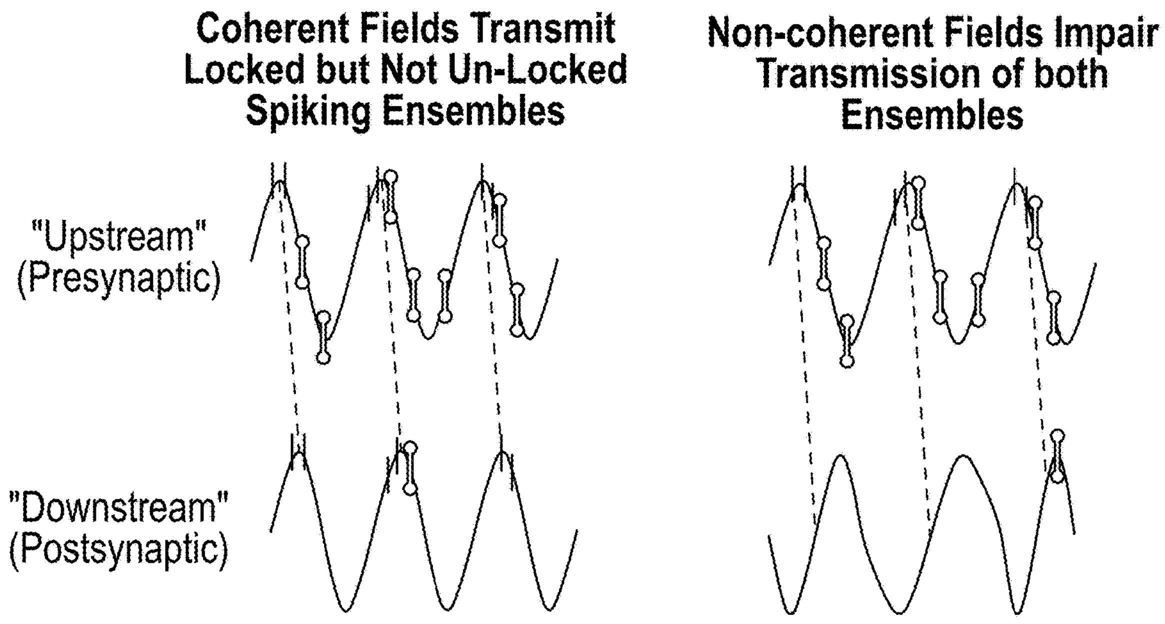
FIG. 1B is a schematic illustration of a physiologic mechanism according to aspects of the present disclosure.

FIG. 1B is a schematic illustration of the physiologic mechanism described above. The notion of state can be a representation of the current environment, the available actions, and the likely outcomes of those actions. This type of contextual information is essential for engaging in flexible behavior (e.g., frequent reversals performed in a Bandit task). Without state representations, learning can devolve onto stimulus-response habits that do not support reversal. These state-dependent processes are dysfunctional in inflexibility disorders and are encoded in spiking ensembles within multiple prefrontal structures. Further, synchrony (e.g., coherence) of low-frequency LFP oscillations between brain regions can be a general mechanism for inter-regional communication, as is locking of spiking activity to the LFP. As such, flexible behavior requires these state-encoding PFC ensembles to phase-lock to their local low-frequency LFP (e.g., shown as grey spikes from the perspective of FIG. 1B), and for that LFP to be coherent between regions. Failure of spike-field locking (e.g., shown as black spikes with circular ends from the perspective of FIG. 1B) and field-field coherence can both contribute to failure of the "more flexible" dorsal cortico-striatal loops, which can lead to perseverative/restrictive behavior.

As such, the present disclosure provides systems and methods for measuring and/or augmenting brain activity, specifically activity correlated to flexible/inflexible behavior, using stimulation, such as electrical stimulation. The electrical stimulation and monitoring can be done via the system described herein.

Figure 2:
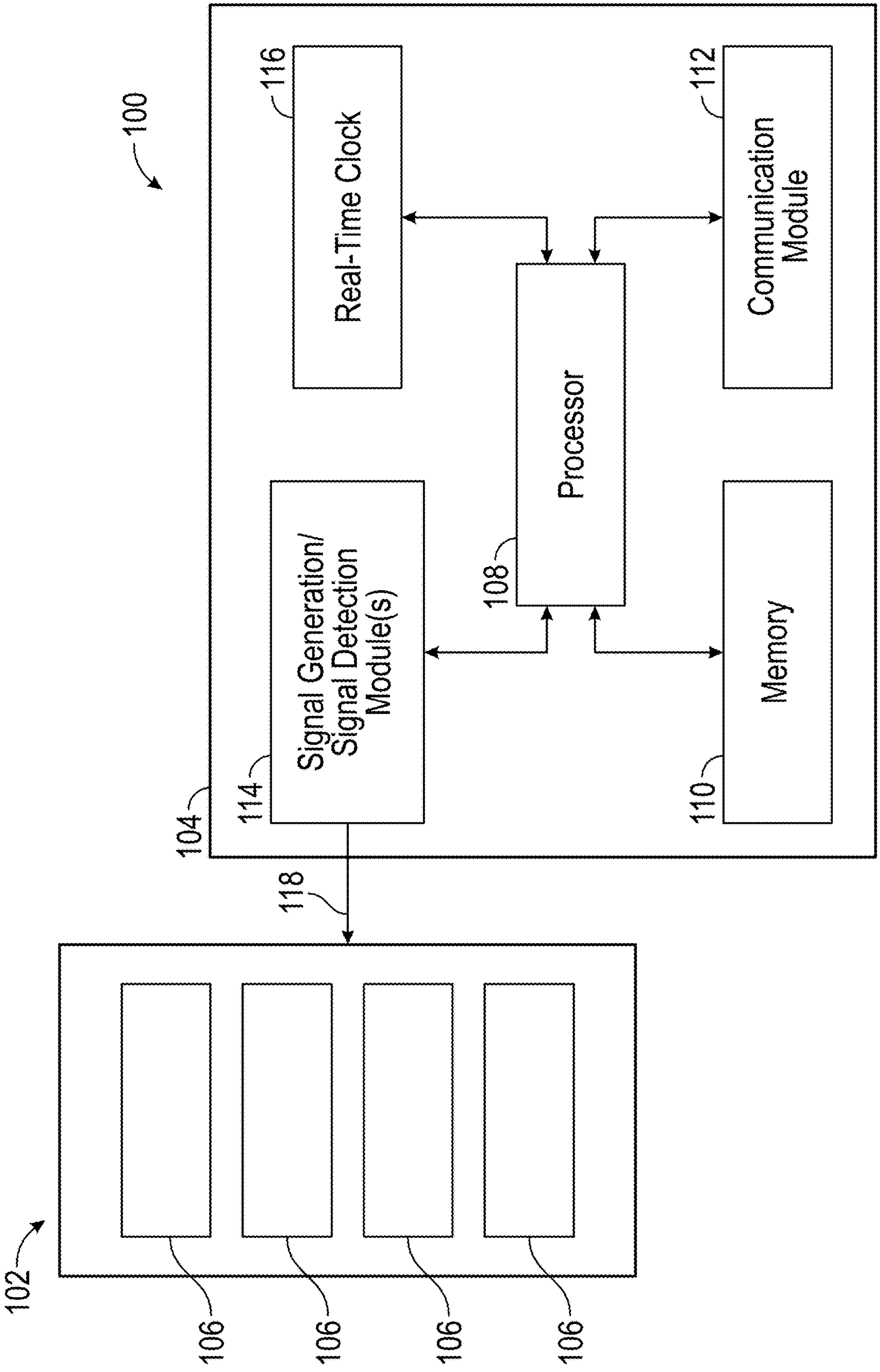
FIG. 2 is a schematic illustration of an exemplary stimulation system.

FIG. 2 is a block diagram of a non-limiting exemplary stimulation system in accordance with the present disclosure. As shown, the stimulation system 100 may generally include a stimulation assembly 102 and a controller 104 in communication with the stimulation assembly 102. The stimulation assembly 102 may include a number of stimulators 106 configured to deliver stimulations to control brain activity in the subject. The stimulators 106 may include various electrodes, or probes with electrical contacts, configured for delivering electrical stimulations to the subject. Some non-limiting examples may include micro electrodes, deep brain stimulation (DBS) electrodes, electrocorticography (ECoG) arrays, electroencephalogram (EEG) electrodes, high-density silicon probes, and the like. In some implementations, the stimulators 106 may be configured to provide other types of stimulations, including magnetic stimulations and ultrasound stimulations. For example using magnetic stimulation coils, and optical stimulations, for example, using optogenetic fibers, actuators, ultrasound devices, and the like. In addition, the stimulation assembly 102 may also include various detectors or sensors capable of measuring brain activity in the subject. Non-limiting examples include electrical leads or contacts, magnetic detectors, optical detectors, and so forth. The stimulation assembly 102, or stimulators 106 therein, may be wholly or partially implanted in a patient's skull, scalp, or both. In other implementations, the stimulators 106, may be positioned on the subject but not implanted. Depending on the mode of stimulation, the stimulation assembly 102 may also utilize various methods and structures to support and couple the stimulators 106 and detectors to the subject.

The controller 104 may generally include a processor 108, a memory 110, such as flash or other type of memory, a communication module 112, signal generation/signal detection modules 114, a real-time clock 116, and optionally a power source (not shown). As shown, the controller 104 may also include various connections, or terminals 118 for transmitting signals generated by the signal generation module 114. Any or all of these elements may be implanted into a patient's body or carried/worn externally to the body, or some elements may be used in each configuration with an appropriate interconnection system.

In some implementations, the controller 104 may also include an input for accepting user selections, operational instructions and information, as well as an output or display for providing a report. Specifically, the input may include various user interface elements, such as a mouse, keyboard, touchpad, touch screen, buttons, and the like. The input may also include various drives and receptacles, such as flash-drives, USB drives, CD/DVD drives, and other computer-readable medium receptacles, for receiving various data and information. To this end, the input may also include various communication ports and modules, such as Ethernet, Bluetooth, or WiFi, for exchanging data and information with various external computers, systems, devices, machines, mainframes, servers or networks.

The processor 108 may be configured or programmed to perform a variety of functions for operating the controller 104 using instructions stored in memory 112, in the form of a non-transitory computer readable medium, or instructions received via input. In some implementations, the processor 108 may control the sending and receiving of instructions and operational parameters (for example, via a wireless transcutaneous link in the communication module 112), the storage of the operational or stimulation parameters and instructions in memory 110, the transmission of the operational parameters to signal generators in the signal generation module 114, the selective triggering of the signal generators to provide electrical, and other stimulations, to various brain regions or tissues of a subject, as well as synchronizing various functions using the real-time clock 116. For instance, the processor 108 may communicate with the real-time clock 116 to determine the timing, phase lag, and synchronization of various stimulations. The processor 108 may also communicate with the real-time clock 116, as well as other hardware and digital logic circuitry, to accurately store activation times in memory 110 and provide activation counts. By way of example, the processor 108 can be a programmable microprocessor or microcomputer.

The signal generation module 114, in communication with the processor 108, may include a number of signal generators for providing activating signals to the stimulators 106. In some implementations, each of the stimulators 106 may be individually controlled using separate signal generators. The signal generators can be independently operated, either sequentially or concomitantly, by the processor 108, to provide stimulation signals with various intensities, frequencies, phases, pulse widths, durations and waveforms. In one embodiment, the signal generators may be controlled to provide stimulations. In addition, in some implementations, the signal generation module 114 may include an output sensing circuit to monitor contact output, as well as other fail-safe mechanisms. This may be desirable, for instance, in order to mediate timed switching for biphasic pulsing.

The signal detection module 114 may include various hardware, and be configured to detect brain signals acquired using the stimulation assembly 102. For instance, the signal detection module 114 can include various analog-to-digital converters, voltage/current meters, amplifiers, filters, and other elements. Signals from the signal detection module 114 may then be provided as input and processed by the processor 108. Alternatively, the signals may be stored in the memory 110 and subsequently accessed/processed by the processor 108.

In some aspects, the processor 108 may receive signals corresponding to brain activity in one or more regions of a subject's brain as input. The processor 108 may then analyze the signals, for example, to determine a synchrony between two or more regions, for example, by computing various metrics indicative of synchrony, such as coherence and others or to determine (or detect) a phase of oscillation of one or more regions. In some aspects, the processor 108 may receive such information from various input elements configured on the controller 104, as described, or alternatively from an external or remote device, computer or system, by way of the communication module 112. The processor 108 may also access a reference or database, as described, stored locally in the memory 110, or at storage location. In some implementations, the processor 108 may operate in an open-loop or a closed-loop fashion to control brain activity in a subject.

In some implementations, the controller 104, along with the stimulation assembly 102, may be part of a standalone stimulation system. Alternatively, the controller 104 may be a wearable or implantable unit that is programmable or configurable using an external device, computer or system. To this end, the communication module 112 may be configured to send and receive various signals, as well as receive power. Specifically, the communication module 112 may include an antenna, or an input-output wire coil, a receiver and transmitter, data converters, as well as other hardware components. As a non-limiting example, the receiver and transmitter may be configured to receive and transmit radio-frequency (RF) signals. In some implementations, the antenna may be configured for transcutaneous wireless two-way communication with an external wearable device, sending and receiving signals when the external wearable device is placed in close proximity. The communication signals may be transmitted through magnetic induction and include information for operating and/or programming the processor 108. For instance, the communication signals may include triggers or command signals for generating stimulations. In some aspects, transmitted signals may also be configured to power or recharge battery components powering the controller 104. The antenna may be connected to a receiver and transmitter, which in turn may be connected to serial-to-parallel and parallel-to-serial data convertors, respectively. Any information sent or received, as described, may then be processed by the processor 108.

As mentioned, the controller 104 may be powered by an internal and/or external power source. For example, an internal source may include a standard rechargeable battery, comparable to batteries used in implantable devices (e.g., pacemakers). Alternatively, or additionally, the internal power source may include a capacitor in combination with a regulator, such as a single ended primary inductor converter or dc-dc converter, that together can generate a constant current or voltage output for short periods of time. In some implementations, the capacitor may be charged by an external wearable device. As such, the controller 104 may include an induction coil, or thin, tightly wound wire that allows for RF telemetry and/or battery recharge by an external wearable device, configured either as part of the communication module 112, or as separate hardware. Other methods of charging may also be utilized.

Figure 3:
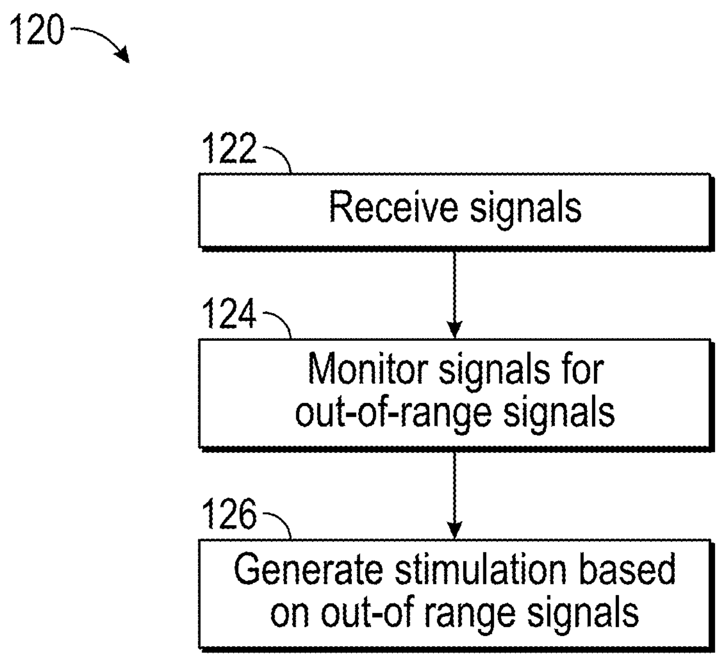
FIG. 3 is a diagram of a stimulation method according to aspects of the present disclosure.

FIG. 3 illustrates a diagram for a method for utilizing the system described herein. In the illustrated non-limiting example, behavioral and/or physiologic signals can be received by the processor 108. The behavioral signals can be received from sensors or other systems in communication with the processor 108. In one non-limiting examples, behavioral signals correlating to task performance can be measured by the real-time clock 116 to measure the reaction time of a subject's response while performing a task. The physiologic signals can be received from at least one source region (e.g., one or more source regions) of the subject's brain at step 122 (e.g., regions involved in cortico-striatal circuits). In one non-limiting example, the source regions may include one or more of the lateral prefrontal cortex, medial prefrontal cortex, orbitofrontal cortex, amygdala, cingulate cortex, insula, hippocampus, dorsal medial striatum, ventral medial striatum, and basal ganglia. The physiologic signals can be received using the signal detection module 114 via the detectors of the stimulation assembly 102.

At step 124, the processor 108 can monitor the received signals. According to one non-limiting example, behavioral signals correlating to the task performance of the subject can be monitored. According to another non-limiting example, physiologic signals from the source region can be monitored in one or more predetermined frequency bands (e.g., the theta and/or alpha bands) to determine if at least one signal of the received signals is indicative of an out-of-range behavioral flexibility. In another non-limiting example, the processor 108 can monitor the received physiologic signals from the source region in the 0-250 Hz frequency range to determine if any one or more of the physiologic signals indicates an out-of-range behavioral flexibility. In one non-limiting example, the processor 108 can be configured to monitor synchrony between multiple regions of the brain. In one non-limiting example, the monitoring of the one or more brain regions may include measurements of oscillatory activity within the lateral prefrontal cortex, medial prefrontal cortex, orbitofrontal cortex, amygdala, cingulate cortex, insula, hippocampus, dorsal striatum, ventral striatum, and basal ganglia. The one or more brain signals from the one or more brain regions may include oscillatory synchrony in the theta and alpha bands between cortical regions, striatal nuclei, and cortex to striatum. As such, the stimulation system 100 can be configured to monitor the synchronization of signals among a plurality of regions of the brain. In one non-limiting example, means of determining the out-of-range flexibility (e.g., an out-of-range oscillatory synchrony) can include measuring coherence, phase lag index, cross-frequency coupling, phase-amplitude coupling, amplitude correlation, and the like. In other non-limiting examples, synchrony may be computed through a causality measure (e.g., a Granger causality) or a cross-frequency metric such as a modulation index. In one non-limiting example, a state of increased flexibility may be associated with increased theta synchrony between the one or more regions of the brain. For example, between the dorsal prefrontal cortex and the dorsal medial striatum). In another non-limiting example, a state of decreased flexibility may be associated with increased theta synchrony between the one or more regions of the brain. For example, between the ventral prefrontal cortex and the ventral medial striatum. One of ordinary skill in the art would recognize that the above examples for determining states of flexibility are only two non-limiting examples of state determination. Further, the model for determining the state may be customized to the brain regions most representative of an individual subject's dysfunction.

At step 126, the processor can control the signal generation module 114 to generate a stimulation pulse (or series of pulses) based on the sensed out-of-range behavioral flexibility. The stimulation pulse(s) generated by the signal generation module can be configured to be delivered to at least one target region (e.g., one or more target regions) of the subject's brain via stimulators 106 in the stimulation assembly. In one non-limiting example, the target region can be the same as the source region. In another non-limiting example, the target regions may include one or more of the lateral prefrontal cortex, medial prefrontal cortex, orbitofrontal cortex, amygdala, cingulate cortex, insula, hippocampus, dorsal medial striatum, ventral medial striatum, and basal ganglia.

Figure 4:
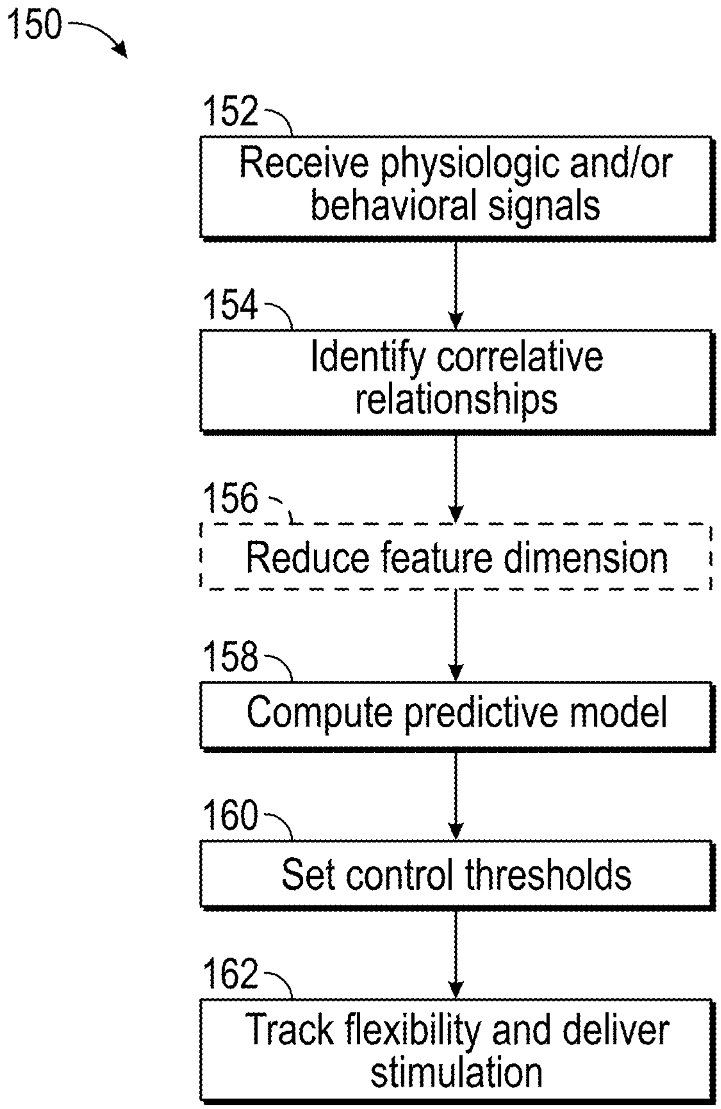
FIG. 4 is a diagram of a stimulation method according to another aspect of the present disclosure.

Expanding on the method described with respect to FIG. 3, FIG. 4 illustrates a method 150 for identifying when signals related to flexibility are out of a desired range, and then providing responsive stimulation based on those out-of-range signals. Specific non-limiting examples of which will be described further with reference to the figures following FIG. 4. Similar to the method described in FIG. 3, signals can be received by the processor 108. The received signals can include simultaneous acquisition of physiologic signals and behavioral signals. According to other non-limiting examples, the received signals can solely include behavioral signals. Physiologic signals (e.g., neural signals from a source region) can include a wide range of brain signals as previously described above with respect to FIG. 2. The physiologic signals can also include signals from other body organs other than the brain (e.g., skin conductance or heart signals) sensed from other sensors in and on the body. Behavioral signals can be any aspect of human behavior that can be captured and quantified. According to some non-limiting examples, behavioral signals can include classifications of the type of activity a patient is trying to do in each instant of a recorded time period (e.g., cognitive tasks and others described below with respect to FIGS. 6A-6D), performance on a standardized behavioral task or assay (e.g., reaction time and others described below with respect to FIGS. 8-10), bodily motion or derived aspects of that motion quantified by worn, carried, or implanted sensors, and/or measures of behavioral flexibility/variability derived from voice analysis and/or analysis of text entered into a computing device.

In some non-limiting examples, combinations of these behavioral signals can be the most appropriate way to measure the clinically relevant form of flexibility. The duration of data collection can vary between a second to many days. The duration of data collection can be determined by the mathematical structure of the model chosen (e.g., based on the number of free parameters), the variability and signal-to-noise ratio of the available signals, and the specific forms of stimulation chosen for the given clinical instantiation.

In some non-limiting examples, behavioral signals might be transformed to extract features that are particularly relevant for analysis or particularly predictive of a phenomenon of interest. As described below in reference to FIGS. 9-11, this may include extracting sub-components through a state-space filter or other latent variable model. Other non-limiting examples might include change scores or derivatives of a behavioral signal, variance of that signal in a specified time period, linear or non-linear mixtures of multiple signals (e.g., as derived from a component analysis), or coefficients of a mathematical model fit to the behavioral data.

With continued reference to FIG. 4, upon receiving the signals at step 152, the processor 108 can then identify correlational relationships between the acquired physiologic signals and behavioral signals at step 154. In some non-limiting examples, laid out further below, this may be achieved by computing correlation coefficients or univariate regression coefficients between the two time series. Any mathematical operation that describes the predictive relation between two time series may be used. This may be referred to as an “encoding” or “decoding” model, which is mathematically equivalent to a regression. According to some non-limiting examples, in cases where time series are sampled at different rates, the time series can be co-registered by a variety of processes, non-limiting examples of which include interpolation, filtering, point process/rate function modeling, or kernel smoothing. In other non-limiting examples, correlative relationships may be determined by curve or basis function fitting, statistical variance analysis, distance metric evaluation, and other forms of statistical model fitting.

According to some non-limiting examples, the method 150 can optionally reduce the available signals to a lower-dimensional set of features at step 156 (e.g., minimizing the feature number). In two non-limiting examples described below with respect to FIGS. 6D-6C and FIG. 11C, this can be achieved by stepwise selection of signals/features for inclusion in a final model. Variables may be selected either by adding them to an iterative model or removing them from an already fitted larger model. The criterion for such inclusion or removal may be a measure of performance improvement, and it may further be one that protects against overfitting, such as an information criterion or a metric on a held out portion of the dataset. In other non-limiting examples, ensemble methods, voting methods, or importance scoring may be used for selection. In other non-limiting examples, a regularization or shrinkage method may be applied to a fitted model. In other non-limiting examples, customized objective functions may be created, which may combine any of the foregoing selection criteria with cost scores that penalize the computational effort or power required to compute or track a given signal. This may be particularly advantageous if the physical realization of the block diagram of FIG. 2 is an implanted medical device or other system with a limited memory and/or processor architecture. It may not be required that the objective function have any specific mathematical properties, nor that an algorithm be used that is guaranteed to converge to a global optimum.

Upon the identification of the correlative relationships in step 154, the processor 108 can convert the features/signal correlations to a predictive model at step 158 that will track and estimate the behavioral quantity of cognitive flexibility when provided with new values of the physiologic signals. This may also be referred to as a “decoding” or “classification” operation, a term which is mathematically equivalent. In one non-limiting example described below with respect to FIGS. 6A-6D, the predictive model can consist of training of a classifier to predict whether a patient is or is not engaged in an effort to flexibly alter his/her thinking. In another non-limiting example described below with respect to FIGS. 9A and 11A, the predictive model may consist of fitting an optimal state-space filter. In another non-limiting example described below with respect to FIG. 5, the predictive model may be a regression model (which may be computed over a sliding window/delay taps on the time series data). According to other non-limiting examples the predictive model can be a linear or non-linear filtering transform, an ensemble method such as a particle filter, forest of decision trees, or majority-vote method, an autoregressive model, a classifier based on a discriminant function with or without transformation of the input variables through non-linear functions, or an artificial neural network.

Once the predictive model has been calculated, control thresholds can be identified at step 162 to define the acceptable range for the estimate of cognitive flexibility derived by the predictive model. The method of setting the threshold may be defined by the specific behavioral signals to be tracked, their signal to noise ratio, estimates of the ranges usually occupied by the tracked signal, goals of the clinician and/or patient, the specific type of stimulation to be applied (e.g., whether there are greater risks of over- vs. under-stimulation), an energy budget (e.g. set by the available battery for stimulation between recharges), and the relative rate of change of the behavioral signals. As described below with respect to FIG. 10, in one specific non-limiting example, the acceptable ranges can be set based on a clinician's judgment of the range occupied by behavioral or physiologic signals. In some non-limiting examples, the range thresholds may be set to define a "dead band" in which no stimulation should be applied.

Lastly, at step 162 of the method 150, new samples of the physiologic and/or behavioral signals are acquired and transformed through the predictive model to obtain a new estimate of the current level of behavioral flexibility. This is then compared to the threshold(s) and range(s) as previously described with respect to step 160, and stimulation can be delivered when the specified range is exceeded.

This process can be repeated a plurality of times in a given treatment period. As noted, stimulation may be delivered according to a wide range of policies. In one non-limiting example shown below, clinician-determined stimulation parameters may be delivered in an on-off or ramped fashion when the specified range is exceeded. In other non-limiting examples, multiple stimulation parameters may be adjusted as continuous variables, in response to the degree to which the current flexibility estimate deviates from the specified threshold(s) and range(s). In some non-limiting examples, the thresholds may be defined as fuzzy or soft, such that control is applied to the system fractionally or probabilistically as the flexibility estimate nears a threshold crossing. In some non-limiting examples, a mathematical/computational model of the system response to stimulation may be estimated and/or updated as stimulation is delivered, and the output of this model may be used to compute the nature and parameters of the applied stimulation. In some non-limiting examples, this model may include a categorical look-up table or atlas. Any of the above may include a learning or agent algorithm that develops a stimulation policy by trial and observation. Any of the above may also include clinician-specified or hard-coded limits and lockouts to prevent excessive or unsafe types of stimulation.

As was done in the non-limiting examples laid out below, either physiologic or behavioral variables may be converted to derived quantities at any step in this process, through a variety of mathematical transforms. These may include transformation into a frequency or complex domain, computation of correlation/connectivity/information flow operators, computation of graph operators, or other derived quantities such as the variance or change in other moments of a signal over time.

In some non-limiting examples of the process, the above steps may be repeated at a pre-set interval to re-establish the predictive models. In other non-limiting examples, the system may measure its own prediction error and automatically adapt any of the derived model components. In yet other non-limiting examples, the steps may be repeated as needed based on a patient-reported or system-detected change in clinical status.

By way of example, the present approach was utilized to alter flexibility in brain activity of human models. The examples provided herein are non-limiting.

Figure 5A:
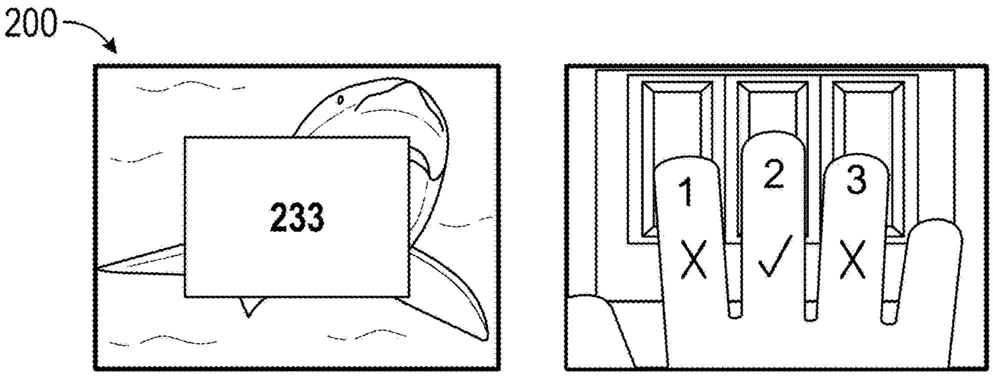
FIG. 5A is an exemplary illustration of a task given to subjects according to aspects of the present disclosure.
Figure 5B:
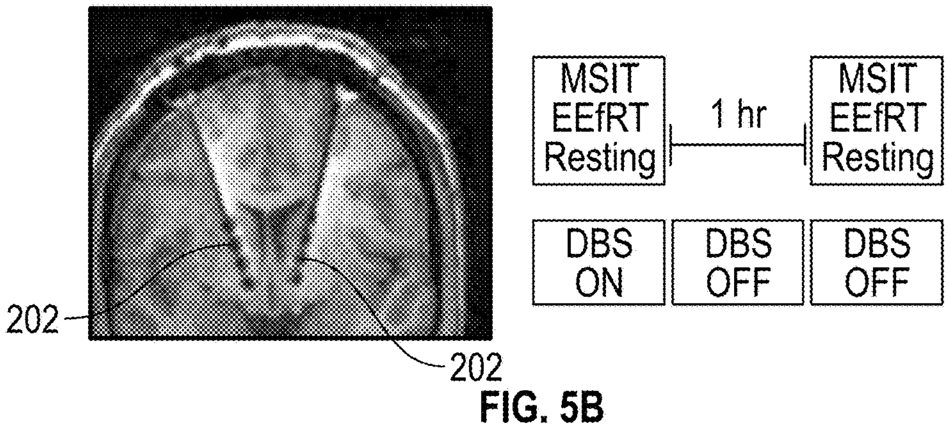
FIG. 5B is a schematic illustration of a task sequence according to aspects of the present disclosure.

FIGS. 5A-5D illustrates one specific example of carrying out the method 150 of FIG. 4 utilizing a regression model as the predictive model. Referring now to FIGS. 5A-5B, the human dorsal striatum can be monitored (e.g., block 152 FIG. 4) and stimulated while patients perform a task requiring flexible decision-making. For example, a patient can perform a Multi Source Interference Task (MSIT) 200. In the affective MSIT 200, in one non-limiting example, subjects can choose a number that differs from neighboring numbers (see FIG. 5A). An underlaid affective/arousing picture from the International Affective Picture System (IAPS) can provide a salient distraction (i.e., a conflict). Further, the motor mapping required to respond correctly is non-intuitive. Switching between these high-conflict interference trials and easier control trials can be done rapidly. Behavioral signals can then be received in the form of response times (e.g., block 152 of FIG. 4) to index subjects' capability for flexibly ignoring both distractors and prepotent motor responses.

Referring now to FIG. 5B, subjects with deep brain stimulators (DBS) 202 in the ventral internal capsule can perform the affective MSIT 200 and other tasks with their DBS stimulators 202 both on and off and with simultaneous EEG recording. Between task/recording sessions, DBS was off for a predetermined period of time to emphasize stimulation-off effects (e.g., one hour). Note that the fibers targeted by DBS are that of cortico-striatal connections (see FIG. 5B).

Figure 5C:
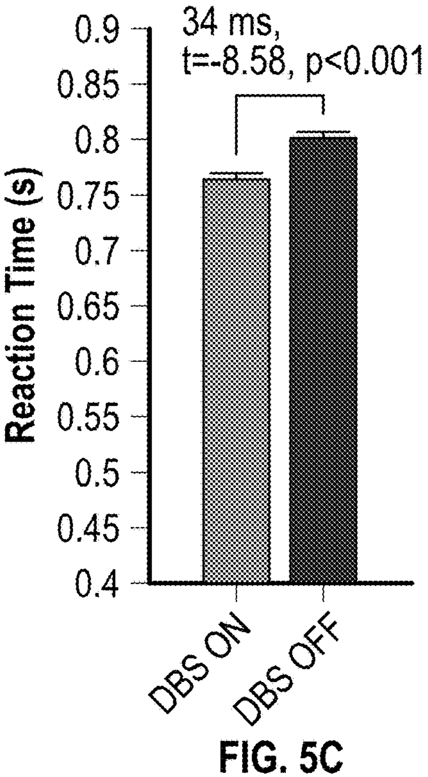
FIG. 5C is a graph illustrating exemplary results of reaction times.
Figures 5D, 5E, 5F:
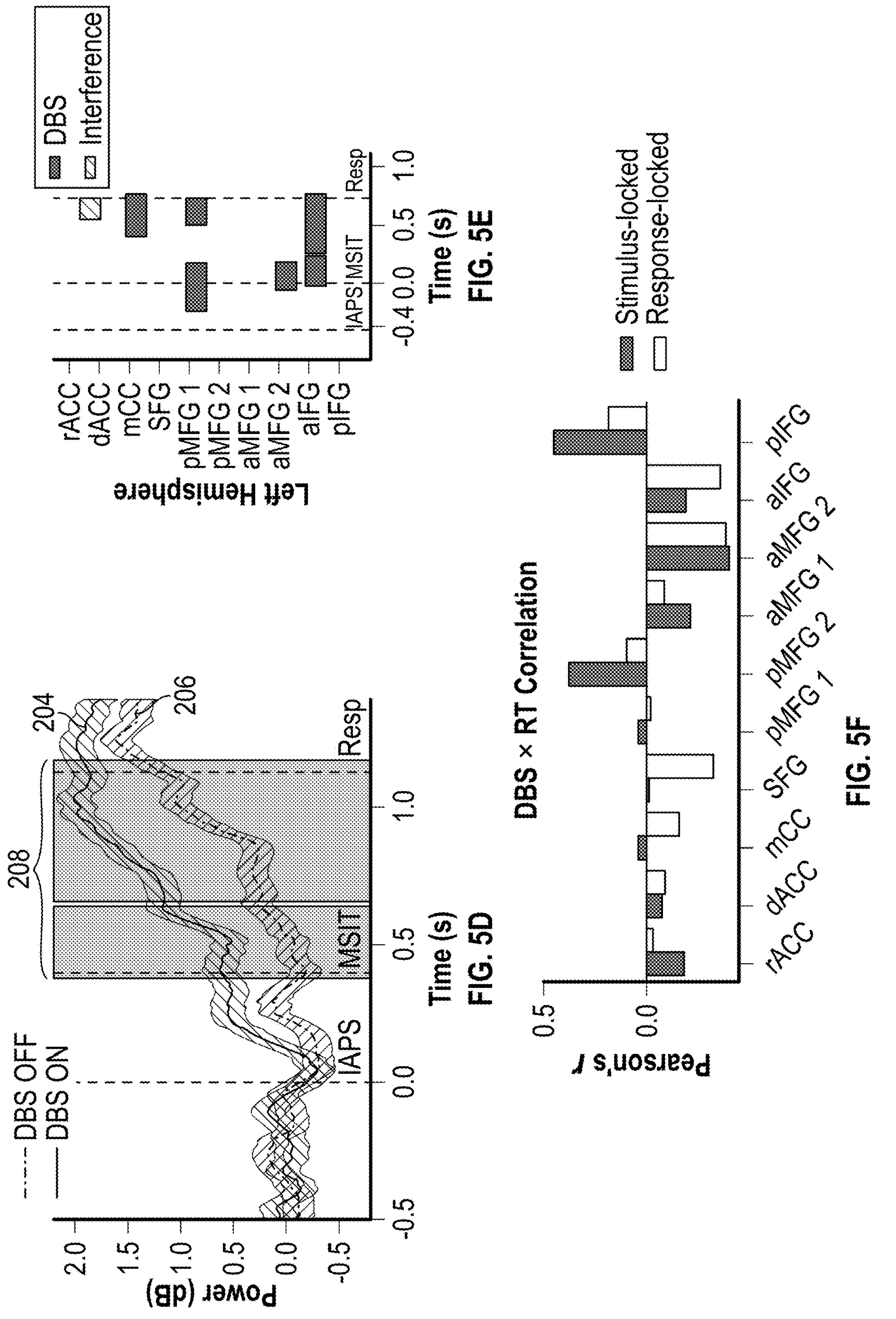
FIG. 5D is a graph illustrating exemplary results of low-frequency oscillations.
FIG. 5E is a graph illustrating exemplary results of theta power difference in specific PFC regions.
FIG. 5F illustrates a graph of a regression model fit to predict task performance from physiologic signals of theta power recorded from brain regions.

FIGS. 5C-5E show example graphs illustrating results of using stimulations in the human model in accordance with various embodiments. FIG. 5C illustrates that stimulation can enhance decisional speed without increasing errors, which can be a sign of increased flexibility. Response times were a mean of 34 ms faster with DBS ON. This was not accompanied by an increase in errors and subjects were not faster on tasks requiring simple motor responses, which shows that the effect is a specific augmentation of flexible, top-down cognitive processing through stimulation of cortico-striato-thalamic fibers.

Looking towards FIG. 5D, the illustrated graph shows that stimulation ON can increase task-related theta power throughout PFC. DBS caused a specific increase in theta oscillations. Shown is theta (5-8 Hz) power of EEG source-localized to the inferior frontal gyms, with DBS ON (shown as curve 204) and DBS OFF (shown as curve 206). Performing a cognitive conflict task can evoke high theta activity specifically during cognitive processing (e.g., after the MSIT stimulus onset). DBS significantly enhanced this effect. The grey shaded region 208 shows clusters of ON-OFF with a significant difference.

FIG. 5E illustrates that these effects can generalize across PFC. Each black bar represents a significant cluster of ON-OFF theta power difference within a specific PFC region; the bar with cross hatching represents a significant interference/conflict effect in cingulate. The differential timing of these effects show earlier processing in middle frontal gyms, later in inferior, and latest in mid-cingulate cortex. The legend for the Left Hemisphere is as follows: a/A, anterior; d, dorsal; I, inferior; m/M, medial; r, rostral; S, superior; CC, cingulate cortex; FG, frontal gyms. In general, these theta oscillatory results depicted in FIGS. 5C-5E reflect network processing and coherence consistent with the physiologic mechanism described above with reference to FIG. 1B.

Taken FIGS. 5C to 5E together, a correlation can be identified between neural signal responses and behavioral signals (in the form of response times), in line with block 154 of the method 150 of FIG. 4. For example, the theta power relationships depicted in FIG. 5 demonstrate a correlative relationship, wherein increased behavioral flexibility is demonstrated by reduced reaction time on the affective MSIT, and wherein the physiologic correlate is increased theta power in multiple areas. With reference to block 158 of FIG. 4, a predictive model in the form of a regression model may then be fit to predict task performance from the physiologic signal of theta power recorded from the brain regions specified in FIG. 5E. FIG. 5F shows an example of such a model. Each bar of FIG. 5F represents a model in which the task response time is predicted as a function of the theta power induced by DBS. The coefficients of the predictive model are expressed as Pearson correlation coefficients, and are sufficiently large to enable prediction. An obvious next generalization of this model would be a multi-regional regression where theta power is combined across the regions for better prediction. With reference to blocks 160 and 162 of FIG. 4, when the predicted task performance falls below a specified threshold, DBS may be given to the ventral internal capsule.

FIGS. 6A-6D illustrates one specific example of carrying out the method 150 of FIG. 4 utilizing a classifier model as the predictive model. Flexible action can require the coordinated activity of multiple structures in the cortico-striatal loops. In one non-limiting example, physiologic signals can be recorded from multiple PFC and striatal sites as patients perform the same cognitive conflict task. Task performance (i.e., operating in a more flexible cognitive mode) can be monitored and distinguished by higher network connectivity among multiple prefrontal structures and dorsal/ventral striatum.

Figure 6A:
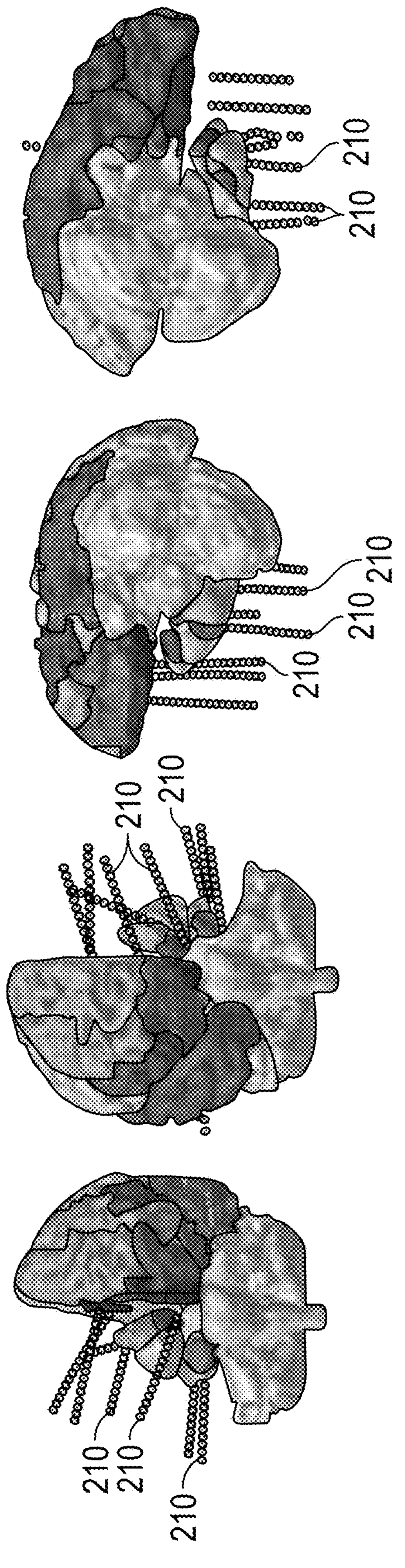
FIG. 6A is an exemplary illustration of a data recording schema according to aspects of the present disclosure.

FIG. 6A illustrates results of subjects with treatment-refractory epilepsy, where the subjects performed cognitive tasks while undergoing invasive electrode mapping for seizure localization. Shown are the electrode shanks 210 from an example subject, demonstrating dense coverage of frontal and temporal cortices as well as some striatal nuclei.

Figure 6B:
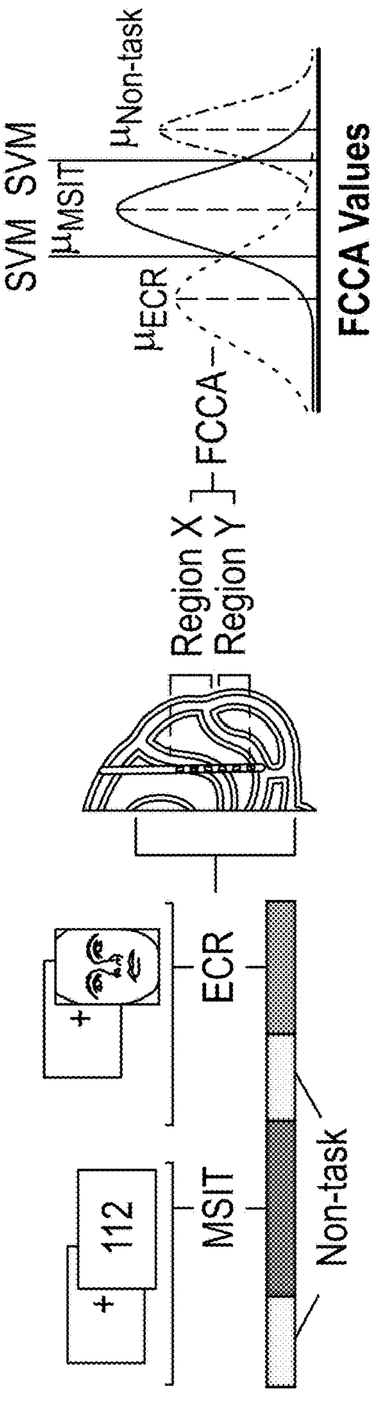
FIG. 6B is an illustration of an experiment and analysis paradigm according to aspects of the present disclosure.

FIG. 6B is an illustration of the experimental paradigm. Subjects performed MSIT (e.g., the same task as shown in FIG. 5A without the affective distractors) and a related conflict task, Emotion Conflict Resolution (ECR). In this case, behavioral signals can be in the form of task performance (reaction time) or classifications of the type of activity the subject is trying to do in each instant of a recorded time period (e.g., MSIT or ECR) while physiologic signals are collected from source regions of the subject (e.g., block 152 of FIG. 4). As in FIG. 5A-B, interference and control trials were interleaved to require rapid response switching, a type of flexibility. To generate a predictive model, fixed-operator canonical coherence (FCCA) between sets of electrodes representing different cortical/subcortical parcels were computed. FCCA computes coherence after transforming sets of electrodes with a principal component operator, to account for differences in the number of electrodes in each brain region. FCCA values were then labeled based on the active task and non-task rest periods and trained a Support Vector Machine (SVM) classifier, which can be utilized as another way to identify correlative relationships between the behavioral signals and the physiologic signals (e.g., block 154 of FIG. 4) and calculate correlation coefficients. In general, this can identify the coherence "edges" that most strongly distinguish task performance from rest. Having identified the strongest coherence edges, the number of features can optionally be reduced by dropping the coherence edges that least strongly distinguish task performance (shown as weighted shading in the connection lines of FIG. 6C).

Figure 6C:
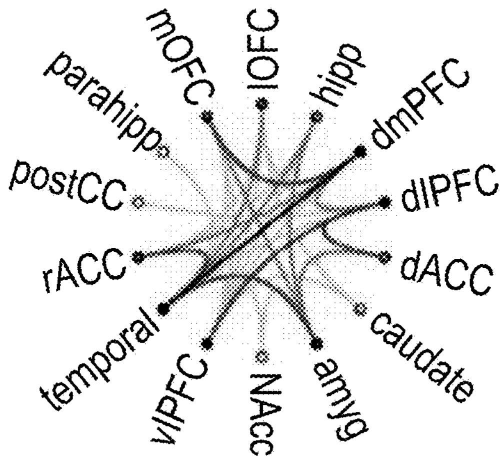
FIG. 6C is a graphical illustration of a spoke diagram demonstrating connectivity between multiple brain regions inferred from oscillations.

FIG. 6C illustrates an exemplary edge-weight diagram showing that cortico-striatal networks are active during flexible decision-making. Each edge in this spoke diagram represents a connection that significantly distinguishes MSIT performance from rest. A dense web of edges connects multiple PFC regions with striatal structures including caudate and nucleus accumbens. The legend for the exemplary spoke diagram is as follows: NAcc, nucleus accumbens; amyg, amygdala; caudate; hipp, hippocampus; dACC, dorsal anterior cingulate cortex; dlPFC, dorsolateral prefrontal cortex; dlPFC, dorsomedial prefrontal cortex; insula; lOFC, lateral orbitofrontal cortex; mOFC, medial orbitofrontal cortex; postCC, posterior cingulate cortex; temporal lobe; and vlPFC, ventral lateral prefrontal cortex.

Figure 6D:
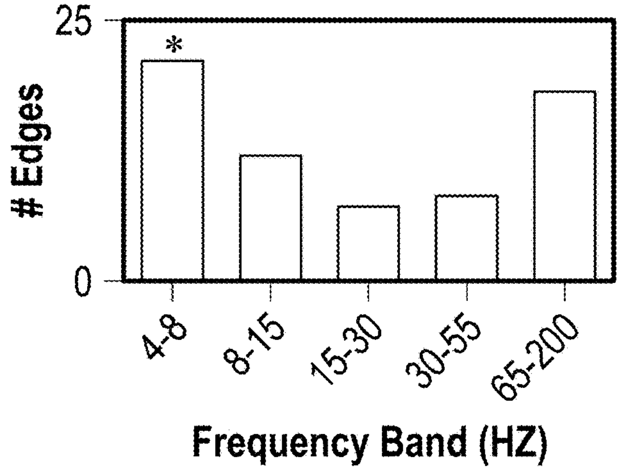
FIG. 6D is a graphical illustration of a bar chart depicting activity across frequency bands and relations of those bands to flexibility.

FIG. 6D illustrates that network coherence during flexible decision-making can be primarily in the theta band. The illustrated bar plot shows the number of edges that corresponded to activity in each frequency band of interest for MSIT vs. non-task classification. After correction for testing of multiple bands, only the theta band (e.g., 4-8 Hz) was chosen significantly more often than would be expected by chance (p=7.6*10−3, binomial test).

Figure 6E:
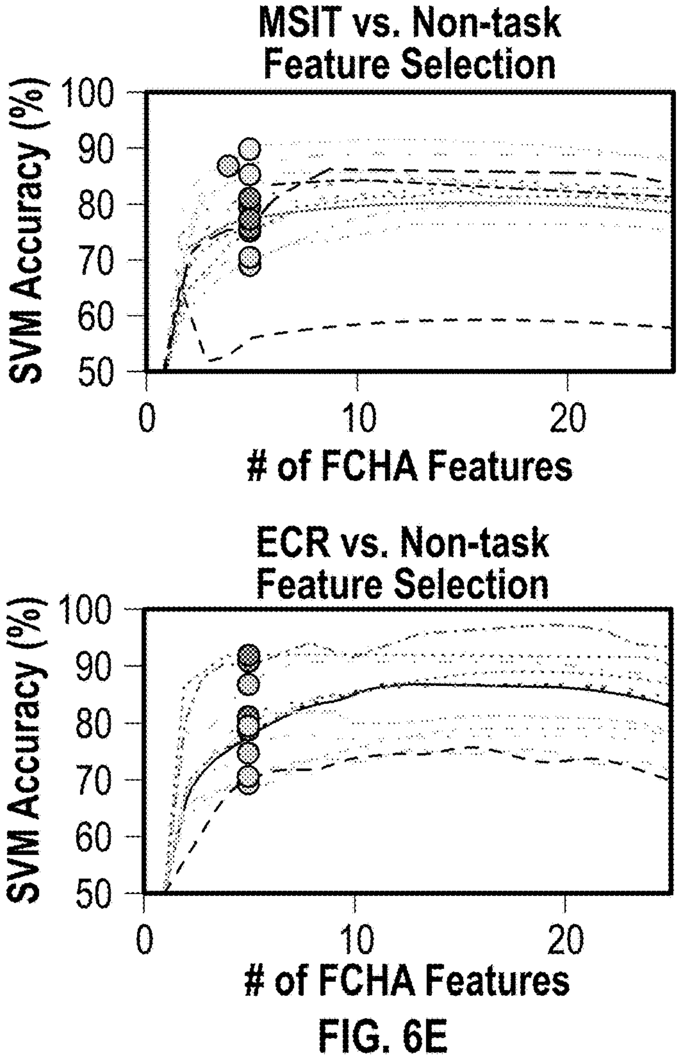
FIG. 6E is a graph illustrating a classification of whether a subject is or is not performing MSIT or ECR tasks.

The above findings can then be used for control of flexibility. A network classification operator as shown in FIG. 6C. represents a correlative relationship and subsequent predictive model as set forth in FIG. 4 at blocks 154 and 158. The canonical correlation and coherence operations illustrated in FIG. 6B represent a dimension reduction as set forth in FIG. 4 step 156. A further dimension reduction may be performed by a feature dropping and validation set analysis, as is illustrated in FIG. 6E. The curves in FIG. 6E demonstrate the classification of whether a subject is or is not performing the MSIT or ECR tasks. Classification is calculated on a held out set of data not used to train the model. Moving from right to left along the illustrated curves, an ever-smaller number of features is used to train the predictive model, and this dimension-reduced model is tested on the validation set. In general, FIG. 6E illustrates that on a held out test set, features may be dropped, such that canonical correlation or coherence between a small number of regions is sufficient for good classification. As is illustrated, as few as 5 canonical correlation or canonical coherence features may be used while still achieving good performance.

Figure 6F:
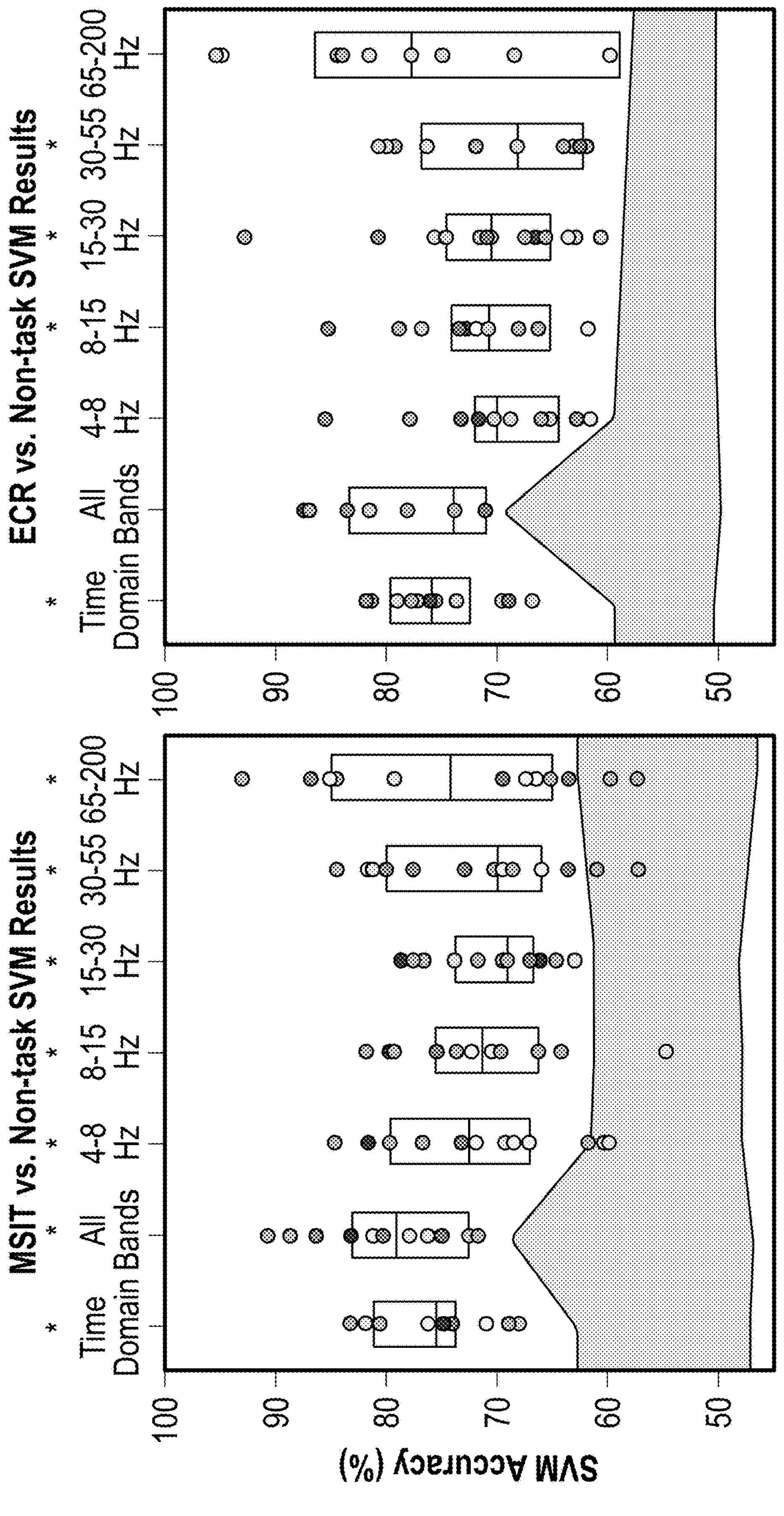
FIG. 6F is a graph illustrating that the predictive model of FIG. 6C can classify whether the subject was or was not performing the MSIT or ECT tasks.

With reference to FIG. 4, step 162, the model may be then applied to new physiologic signals originating from the set of brain regions set forth above, and will yield a prediction of the probability that the subject is currently attempting to engage in flexible behavior. This is illustrated in FIG. 6F, where a predictive model of this type was able to classify whether a subject was or was not performing the MSIT or ECT task. Each data point in FIG. 6F represents a single subject, and the shaded grey region represents chance-level performance. The majority of subjects are classified well outside the chance region. In general, FIG. 6F illustrates that the predictive model illustrated in FIG. 6C can be applied to predict, with probability greater than chance, whether the subject is or is not performing a conflict task. With reference to FIG. 4 at blocks 160 and 162, when this prediction exceeds a pre-determined threshold (e.g., a 75% probability), stimulation may be activated at the brain sites illustrated in FIG. 5B to improve flexible performance.

As previously described herein with respect to FIG. 2, the processor 108 may operate in an open-loop or a closed-loop fashion to control or alter brain activity in a subject. As previously noted herein, cognitive control (an aspect of flexibility) can be defined as the ability to withhold a default, prepotent response in favor of a more adaptive choice. Cognitive control deficits are common across mental disorders, including depression, anxiety, and addiction. Thus, a method for improving cognitive control could be broadly useful in disorders with few effective treatments. As detailed below, in addition to the systems and methods previously described herein, a closed-loop enhancement of cognitive control by direct brain stimulation is provided. Stimulation can be delivered to internal capsule/striatum in participants undergoing intracranial monitoring as they performed a cognitive control task. A framework is also provided to detect control lapses and stimulate in response. This closed-loop approach can be more effective than open-loop stimulation. Finally, decoding of cognitive control and flexibility state directly from activity on a small number of electrodes is provided. These systems and methods provide an approach to treating severe mental disorders, by directly remediating underlying cognitive deficits.

As detailed below, closed-loop enhancement of cognitive control is demonstrated, which can provide clinical utility. A state-space model was developed for tracking conflict task performance in real time. That model was linked to a closed-loop controller, which enhanced task performance more effectively than a corresponding open-loop paradigm. Finally, the input signal for the closed-loop controller was shown to be derived entirely from brain activity, providing a closed-loop system for treating cognitive control deficits.

Figure 7A:
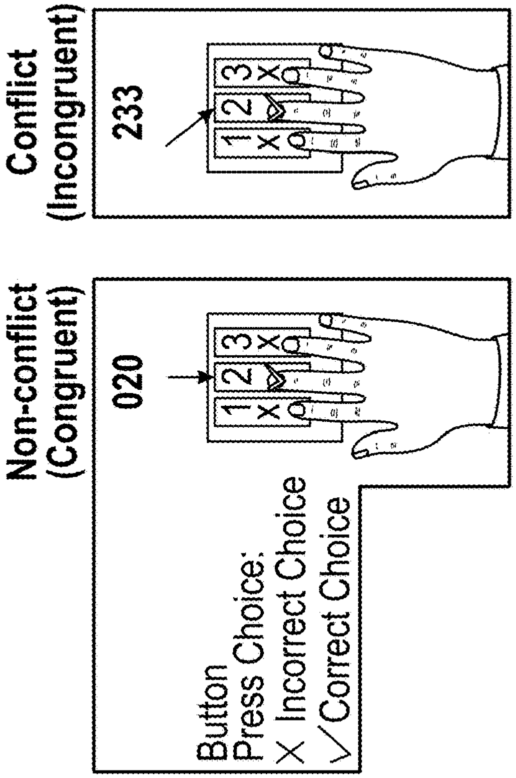
FIG. 7A is a schematic illustration of a multi-source interference task according to aspects of the present disclosure.

Brain activity can be monitored while subjects perform various tasks. For example, during the monitoring of brain activity, subjects can perform a Multi-Source Interference Task (MSIT) with simultaneous recordings of behavior (e.g., reaction times) and local field potentials (LFPs) from both cortical and subcortical brain structures. MSIT is a cognitive control task known to induce statistically robust subject-level effects, at both the behavioral and neural level. These relatively large effect sizes can amplify the ability to detect stimulation-induced differences, by increasing task-related behavioral and neural signatures. MSIT trials can consist of three numbers between, two of which had the same value (FIG. 7A). Subjects have to identify, via button press, the identity of the number that was unique, not its position. Each trial can contain one of two levels of cognitive interference/conflict. Low conflict or congruent (C) trials have the unique number in a position corresponding to its keyboard button, and flanking stimuli were always '0', which is never a valid response. High conflict, or incongruent trials (I), have the position of the unique number different from the keyboard position (Simon effect). On high conflict trials, the non-unique numbers are valid responses (flanker effect). In some cases, the trial sequence can be pseudo-randomized such that more than two trials in a row never shared the same interference level or correct response finger. This can force frequent strategy shifts and increase attention demands, which in turn increase the need to engage/deploy cognitive control. In some non-limiting examples, each subject can perform 1-3 sessions of MSIT. Each session can consist of multiple blocks of multiple trials (e.g., 32 trials, 64 trials, etc.), with brief breaks in between blocks. During blocks, subjects can be instructed to keep their first through third fingers of their right hand on the response keys corresponding to the numbers 1-3. They can also be instructed to be as fast and as accurate as possible. Stimuli (e.g., the MSIT test images) can be presented for 1.75 seconds, with an inter-trial interval randomly jittered within 2-4 seconds. Stimuli can presented on a computer screen with either Presentation software (Neurobehavioral Systems) or Psychophysics Toolbox.

Figure 7B:
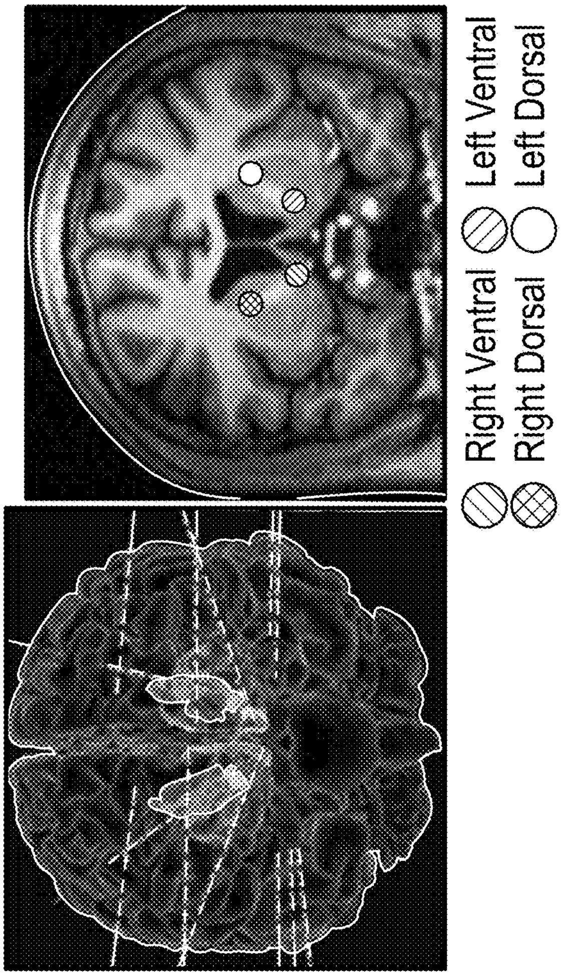
FIG. 7B is a schematic of a typical montage of depth electrodes according to aspects of the present disclosure.
Figure 7C:
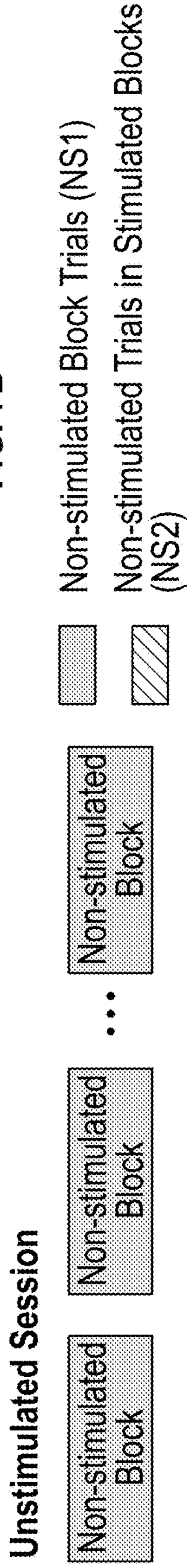
FIG. 7C illustrates an unstimulated trial structure according to aspects of the present disclosure.
Figure 7D:
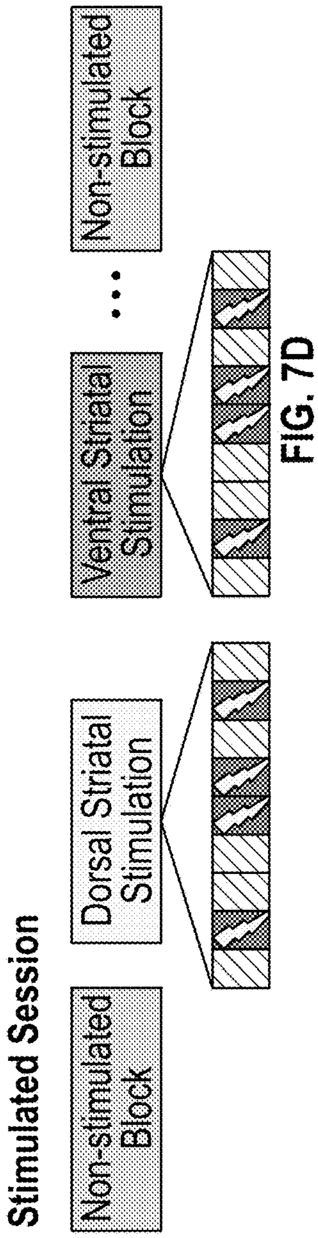
FIG. 7D illustrates a stimulated trial structure according to aspects of the present disclosure.

In an open-loop system, electrical stimulation can be delivered to portions of the brain (e.g., to either the dorsal or ventral internal capsule, and surrounding striatal nuclei, as illustrated in FIG. 7B). In some non-limiting examples, only one site in each block may be stimulated. These stimulation sites can allow a determination of which anatomic sites were most responsible for behavioral effects. In some non-limiting examples, open-loop testing can begin with 1 or 2 blocks of unstimulated trials and end with an unstimulated block (FIGS. 7C-D). FIG. 7C illustrates trial structure during an unstimulated test session. Blocks of trials were separated by brief rest periods. FIG. 7C illustrates trial structure during an open-loop stimulation test session. Some blocks of MSIT trials (e.g., FIG. 7A) had no stimulation at all and are designated NS1, while others had stimulation only on a randomly-selected 50% of trials. Un-stimulated trials in these blocks are designated NS2.

In the illustrated non-limiting example of FIG. 7D, in blocks with stimulation, stimulation occurred on only 50% of the trials. According to some non-limiting examples, stimulation can be a 600 ms long train of symmetric biphasic (charge balanced) 2-4 mA, 90 μs square pulses at a frequency of 130 Hz. Stimulation can be delivered through a neighboring pair of contacts on a single depth electrode (bipolar), with the cathodal (negative) pulse given first on the more ventral contact. Stimulation can be delivered by a Cerestim 96 (Blackrock Instruments), with parameters set manually by a doctor and stimulation triggered by a separate PC that was either delivering or monitoring task/behavioral stimuli. Some specific and non-limiting examples of parameters may include stimulation at 1, 2 and 4 mA, for 1 second, repeated 5 times with 5-10 seconds between each 130 Hz pulse train. The stimulation frequency can be chosen among frequencies most commonly used in clinical DBS for psychiatric disorders. All stimulation was delivered at the image onset during a MSIT task to influence a decision-making process that begins with that onset.

FIGS. 8-12 illustrates one specific example of carrying out the method of FIG. 4 utilizing a state-space filtering model as the predictive model. In a closed-loop system, the stimulation effects on cognitive control can be quantified using a state-space filtering latent variable model to perform subject behavior data analysis. The primary behavior signal of cognitive control can be embodied in a subject's reaction time (RT) to performing tasks (e.g., an MSIT task illustrated in FIG. 7A). As detailed below, this model can separate changes in the baseline/expected reaction times ($x_{base}$) from immediate responses to high conflict ($x_{conflict}$).

First, the effects of stimulation and task factors can be analyzed at the trial level using a generalized linear mixed effect model (GLME):

$$RT \sim \text{Conflict} + blockStim + blockNum + (1|\text{Participant})$$

This and all other GLMEs analyzing reaction time data used a log-normal distribution and identity link function. Fixed effects in the GLME were Conflict (a binary variable coding the trial type as being low (0) or high (1) conflict), stimulation site (blockStim), and block number (blockNum) to account for fatigue or practice effects. Stimulation (blockStim) was coded at the block level, i.e. whether the stimulation site in a given block was dorsal vs. ventral capsule or left vs. right, not whether stimulation was on vs. off on a given trial. Block-level coding was a more parsimonious fit to the data, as determined from information criterion minimization. Participant was a random effect. All categorical variables were automatically dummy-coded by MATLAB's "fitglme" function.

A possible interaction between stimulation and the trial-to-trial conflict level can be tested by fitting an alternate model with an interaction term:

$$RT \sim \text{Conflict} + blockStim + \text{Conflict} * blockStim + blockNum + (1|\text{Participant})$$

This model can be assessed against the primary GLME by comparing model criteria, e.g. Akaike's Information Criterion (AIC), which decreases in models that are more parsimonious fits to the observed data.

To develop closed-loop control and neural decoding strategies, a trial-by-trial estimate of participants' reaction time is needed (e.g., block 158 of FIG. 4). The task is designed to rapidly switch back and forth between trial types, however, reaction time on any given trial is influenced by changes in conflict/interference in addition to (putative) stimulation effects and random variability. This barrier can be overcome using a behavioral state-space modeling framework. The COMPASS toolbox for MATLAB can be used to fit a model that extracts a trial-level estimate of the reaction time independent of conflict effects. This model takes the form:

$$\log y_{RT,k} = x_{base,k} + I_{conflict,k} x_{conflict,k} + \varepsilon_k \quad \varepsilon_k \sim N(0, \sigma_\varepsilon^2) \tag{1}$$

Where $y_{RT,k}$ is the reaction time on trial k, and the $x_k$ are latent, unobserved variables that can be termed "cognitive states". The observation noise, $\varepsilon_k$ would capture other non-structured processes that influence the trial-to-trial reaction time. Note that this model follows the same distribution/link assumptions as the static GLME above. The latent variables were modelled as:

$$x_{base,k} = a_1 x_{base,k-1} + v_{1,k} \quad v_{1,k} \sim N(0, \sigma_{1,v}^2) \tag{2.1}$$

$$x_{conflict,k} = a_2 x_{conflict,k-1} + v_{2,k} \quad v_{2,k} \sim N(0, \sigma_{2,v}^2) \tag{2.2}$$

Where, $a_1$ and $a_2$ define the decay of the state variables over time. $v_{1,k}$ and $v_{2,k}$ are mutually independent white noise processes with zero mean and variance $\sigma_{1,v}^2$ and $\sigma_{2,v}^2$, respectively. That is, it can be assumed that these two processes can vary entirely independently of one another (even though stimulation may influence both).

In the model described above, $x_{base,\ k}$ represents the expected reaction time in the absence of conflict or other external influencing factors, whereas $x_{conflict,\ k}$ represents the expected effect of conflict on the reaction time. $I_{conflict,\ k}$ is an indicator variable, such that $x_{conflict,\ k}$ only affects the expected reaction time on high-conflict trials. $x_{base}$ can be thought of as encoding more general, overarching aspects of cognitive control, such as effortful attentional focus on task stimuli, maintenance of goals in working memory, and preparation to inhibit a prepotent response on incongruent/high-conflict trials. $x_{conflict}$ in that framework, represents the cognitive load of actually deploying the response inhibition in response to conflict. It can be assumed that reaction time follows a log-normal distribution conditioned on the state values. An alternative could be to treat the trial-to-trial conflict effect as fixed across the full experiment, i.e. to only estimate $x_{base}$. In some cases however, internal capsule stimulation might affect both aspects of cognitive control separately, and thus a two-state model to detect that separability was chosen. The goodness-of-fit for that model can be verified by comparing the reaction time residuals to those expected from a white-noise process.

The state-space model assumes that cognitive states are slowly varying, i.e. they show a strong autocorrelation. Thus the GLME cannot be used to analyze stimulation-induced change in these latent variables ($x_{base}$, $x_{conflict}$) because they strongly violate the GLME's assumption that individual datapoints are independent. A non-parametric permutation testing can instead be used, which is well-established as a method for inferential statistics on autocorrelated time-series. The stimulation labels of individual blocks can be shuffled a number of times (e.g., shuffled 1,000 times), with the shuffling nested within individual participants. This can create a distribution of cognitive state values under the assumption of no difference between stimulation sites (or between stimulated and non-stimulated trials). From that distribution, the p-value of the actual state values under stimulation can be inferred. For both the raw reaction time GLME and the cognitive state permutation tests, up to 4 stimulation sites in each participant can be compared to baseline (no stimulation, NS1). Within each analysis, the p-values for these multiple comparisons can be corrected using a false discovery rate (FDR) step-down procedure.

Closed-loop stimulation control can then be performed using the model described above. First, for each subject, model parameters can be estimated using 1-3 days of prior task performance (e.g., prior MSIT performance) without brain stimulation. These parameters can then be provided to a real-time engine that estimates $x_{base}$ and $x_{conflict}$ on each trial. $x_{base}$ which can be considered to track the overall difficulty of sustaining attention and exerting cognitive control (more difficulty leading to longer reaction times), can then be controlled. Cognitive control enhancement can be embodied in a decrease in $x_{base}$. To achieve this, if the estimate on trial k was above a predetermined threshold set by a clinician, the system delivered electrical stimulation at the time of image/stimulus presentation on trial k+1 (e.g., blocks 160 and 162 of FIG. 4). In some non-limiting examples, the threshold can be set based on a doctor's visual assessment, or by computational detection of (e.g., via a processor), of the subject's fastest possible reaction time to attempt a decrease in $x_{base}$ from its unstimulated value. Stimulation parameters and hardware can otherwise be identical to the previously described setup for open-loop stimulation.

For analysis of the closed-loop stimulation results, the complete state-space filtering model estimation can be run offline over the whole dataset, rather than using the less-accurate state values estimated in real time. A key difference is that the offline estimation contains a forward (filtering) and backward (smoothing) pass, allowing future data to influence each trial's estimate non-causally. By considering more information, this offline estimate can more accurately reflect the "true" cognitive process and its change in response to stimulation. To directly compare closed-loop and open-loop stimulation, the state values can be normalized between these two runs such that that the unstimulated blocks in both paradigms had a mean value of 1. That is, both open-loop and closed-loop results can be expressed as change vs. the unstimulated condition on the same day.

By way of another example, as described below a closed-loop approach was utilized to alter flexibility in brain activity of human models. The examples provided herein are non-limiting. As detailed below, the methods described herein can be used to demonstrate closed-loop enhancement of cognitive control, with evidence of clinical utility. In participants undergoing stereotaxic electrode monitoring for epilepsy, internal capsule stimulation is shown as enhancing cognitive control and PFC theta oscillations. A state-space filtering model can be developed for tracking conflict task performance in real time, and that formalism can be linked to a closed-loop controller, which can enhance task performance more effectively than a corresponding open-loop paradigm. In some cases, subjects who self-described as having difficulty with cognitive control reported that stimulation relieved internally-focused, anxious processing and improved their ability to direct their attentional focus, even though they could not detect the stimulation itself. Finally, the examples outlined below can show that the input signal for the closed-loop controller can be derived entirely from brain activity, paving the way for a closed-loop system for treating cognitive control deficits.

Twenty-one participants (age range: 19-57, mean age: 35, female: 12/21, left handed: 5/21) were tested. Study procedures were conducted while participants underwent inpatient intracranial monitoring for seizure localization at Massachusetts General Hospital or Brigham & Women's Hospital. The electrode implants were solely made on clinical grounds and not tailored for research purposes.

The purpose of this study was to show that internal capsule stimulation can enhance cognitive control (shorten response times in a cognitive control task without altering error rates). Local field potentials (LFP) was recorded from a montage of 8-18 bilaterally implanted depth electrodes (FIG. 7B, left). Depth electrodes can had diameters of 0.8-1.0 mm and consisted of 8-16 platinum/iridium-contacts, each 1-2.4 mm long. Electrodes were localized by using a volumetric image coregistration procedure. Using Freesurfer scripts, the preoperative T1-weighted MRI (showing the brain anatomy) was aligned with a postoperative CT (showing electrode locations). Electrode coordinates were manually determined from the CT. Mapping to brain regions was performed using an electrode labeling algorithm. Intracranial recordings were made using a recording system with a sampling rate of 2 kHz (Neural Signal Processor, Blackrock Microsystems, US). At the time of acquisition, depth recordings were referenced to an EEG electrode placed on skin (either cervical vertebra 2 or Cz).

Local field potentials (LFP) were analyzed using custom analysis code in MATLAB (Mathworks) based on FieldTrip. To reduce the influence of volume conduction, LFPs were bipolar re-referenced by subtracting those recorded at consecutive electrode contacts on the same electrode shank. LFP was recorded from electrode pairs spanning 16 brain regions: prefrontal, cingulate, orbitofrontal, temporal, and insular cortices, amygdala, hippocampus, nucleus accumbens, and caudate. All LFP data were decimated to 1000 Hz and de-meaned relative to the entire recording. 60 Hz line noise and its harmonics up to 200 Hz were removed by estimating noise signals through narrow bandpass filtering, then subtracting those filtered signals from the original raw signal. Pathological channels with interictal epileptiform discharges (IEDs) were removed. Such channels were detected with an algorithm that adaptively models distributions of signal envelopes to discriminate IEDs from normal LFP. A Morlet wavelet decomposition was then used to estimate power in 6 frequency bands (4-8, 8-15, 15-30, 30-55, 65-110, and 135-200 Hz) at 10 millisecond time steps. The high gamma (65-200 Hz) band was then fractionated into lower and upper bands to bypass the stimulation frequency at 130 Hz and a 60 Hz harmonic at 120 Hz.

It can be shown that exercise of cognitive control is associated with higher theta (4-8 Hz) power in a fronto-cingulate network, and that stimulation in the internal capsule increases that task-evoked theta. An epoch of 0.1-1.4 seconds after image onset was analyzed, which covers the decision-making period up to the median reaction time. This analysis was focused on non-phase-locked oscillations. From the target epoch, the time-domain evoked response (ERP) can be subtracted. This ERP can be calculated separately for high- and low-conflict trials, and the appropriate ERP can be subtracted from each trial's time-domain data. The time-domain was then transformed to a time-frequency representation. Power in the analysis epoch was averaged within the theta band. For visualization, this power was normalized as a log ratio relative to a baseline period of 0.5 seconds preceding image onset. For analysis, this log transformation can be built into the GLM.

To verify that higher conflict evoked higher frontal theta, the blocks without stimulation can be analyzed. This avoids confounding effects of stimulation and conflict. For each participant, pre-frontal cortical (PFC) channels that had a significant increase over baseline in task-evoked theta (t-test with threshold of $p<0.05$ uncorrected) were selected. For this initial pre-screening step, to avoid a circular analysis, trials were not split into high/low conflict. Rather, channels that showed a theta-band response in general to performing MSIT were identified. In this reduced set of channels, the trials were divided into low and high conflict, then the non-phase-locked theta power was computed. All pre-selected channels in each PFC region were combined, and for each region the GLME was fit:

$$\text{Theta} \sim \text{Conflict} + (1|\text{Participant}),$$

Where Conflict is a binary variable coding the trial type as being low (0) or high (1) conflict. The resulting p-values for testing of multiple PFC regions were then false discovery rate (FDR) corrected.

It was then tested whether open loop capsular stimulation caused a significant increase in theta in the unstimulated trials within a stimulation block (NS2) compared to those in the unstimulated blocks (NS1; see FIG. 7C-D). To accurately assess stimulation effects, stimulation trials that were presumed to be substantially contaminated by artifact were discarded. Then, two types of non-stimulated trials were compared (FIG. 7D). NS1 trials were from blocks in which no brain stimulation was given on any trial. NS2 trials were from blocks with stimulation, but were the pseudo randomly-selected 50% of trials that did not receive stimulation. These NS2 trials were artifact-free, but still showed the behavioral effect of stimulation, and thus should also show physiologic changes related to that behavior change. Therefore, it was tested whether the normalized theta power in NS2 trials was significantly greater than that in NS1, again using a GLME:

$$\text{Theta} \sim \textit{blockStim} + (1|\text{Participant})$$

For this model, one PFC channel was chosen for each participant that had the highest theta during NS2 trials (regardless of conflict level or stimulation site, again to avoid circular analysis). P-values were again FDR corrected to control for testing of multiple stimulation sites against non-stimulation.

As detailed above, a neural decoder was developed for cognitive state variables. A neural encoding-decoding analysis was applied with automatic feature selection. The decoded variables were $x_{base}$ and $x_{conflict}$ from the model in equation (1). The neural features used for decoding were the LFP power, in the above-mentioned frequency bands, averaged over a 2 second interval starting at the MSIT image onset. The analysis was broadened beyond the theta band because, while theta is strongly associated with cognitive control, other frequencies can also carry significant amounts of information about task performance. The 2 second epoch was chosen to include both the response and post-response processing. This wider window produced smoother features with less trial to trial variance, improving decoder stability. Here, data was averaged across a 2 second time interval (200 samples) to get power features per-trial. Similar to the theta analysis, the decoding considered only NS1 and NS2 trials, to prevent the influence of stimulation artifact. The study was focused on LFP spectral power (rather than other potential behavioral covariates such as connectivity/coherence) because power can be efficiently computed within implantable neural devices. Successful decoding from power alone can pave the way for use of these closed-loop controllers in clinical settings.

Decoding analyses were performed with out-of-sample validation, using both stimulated and unstimulated MSIT datasets. For each MSIT session, 50-60% of the total trials were used to fit an encoding model (training set). These consisted of NS1 trials in unstimulated datasets and both NS1 and NS2 trials in the stimulated experimental datasets. The training trials were selected from contiguous blocks that, collectively, covered the full range of the states during an experiment. The encoding model that we used is a linear model of the form $Y_k \sim 1+\beta x_k$, where $Y_k$ is a neural feature and $x_k$ is one of the cognitive states on the k-th trial. A feature was considered to be a candidate for decoding if the modified F-statistic of the corresponding model corresponded to $p<0.01$ (uncorrected). This procedure selected a set of candidate neural features that potentially encoded each cognitive state. The exact number of training trials for each dataset was determined as the minimum required (in the 50-60% range) to have a non-zero number of features selected by the encoding procedure.

Next, to reduce overfitting, the feature set was pruned. This pruning used the 40-50% of the dataset that had not been used for initial feature selection (test set). The posterior distribution of the cognitive state was estimated solely from neural data, through the Bayesian filtering process. The root mean square error (RMSE) was calculated between the neurally decoded state and the "true" (estimated from behavior) cognitive state in this held-out test set. The feature whose removal led to the most improvement in RMSE was then sequentially dropped. The final decoder was then the set of features that survived this dropping step, i.e. where dropping any further feature would increase RMSE on the test set. An important caveat is that the latent cognitive state is itself a multivariate Gaussian estimate. That estimate's value can depend on the starting point of the expectation-maximization process used to fit the state-space model. To control for this, the behavioral estimation was re-ran for each participant 1,000 times with different random seeds, producing 1,000 estimates of the underlying trajectory. The neural decoder's performance was then evaluated based on whether its point estimate of the decoded state was within the confidence interval derived from these multiple trajectories.

This encoding-decoding model was fit separately to data from unstimulated sessions (consisting of only NS1 trials) as well as to stimulated sessions (both NS1 and NS2 trials), to determine how the encoding structure was altered by electrical stimulation. Stimulated trials were not included in this analysis, because there is a prominent stimulation artifact that makes these trials easily discriminable. In cases of stimulation-behavior correlation, behavior could be trivially decoded simply by detecting the artifact.

The results of this research study will now be described. As detailed above, behavioral signals were collected as subjects performed a cognitive control task (the Multi-Source Interference Task (MSIT), FIG. 7A) while undergoing physiologic signal monitoring of a source region (e.g., block 152 of FIG. 4) using invasive electrodes and electrical stimulation in a target region in the internal capsule (FIG. 7B). 8,790 trials were collected across 176 blocks from 21 subjects—12 without brain stimulation, 5 with both unstimulated and open-loop stimulation sessions, 1 with only open-loop stimulation, and 3 with unstimulated and closed-loop stimulation sessions. Dropping incorrect responses and non-responses excluded 345 trials (3.92% of total; 8,445 trials retained in analysis). In open-loop experiments, a random 50% of trials received brief, task-linked stimulation (FIG. 7C-D).

FIG. 8 illustrates that a correlation can be made between behavioral signals and physiologic signals to identify and track the flexibility of a subject, in this case, by illustrating the effect of conflict and open-loop capsular stimulation on cognitive control (e.g., block 154 of FIG. 4). FIG. 8A illustrates changes in flexibility of the subject while performing a task, in this case using behavioral signals in the form of reaction time (RT), during low- and high-conflict unstimulated trials (NS1) from 21 participants. FIG. 8B illustrates the changes in flexibility of the subject while performing a task, in this case using physiologic signals in the form of log theta power ratio, during conflict and non-conflict NS1 trials in frontal regions. Conflict affected flexibility, which is illustrated in the panels of FIG. 8 as slowed response reaction times (a behavioral signal biomarker) and evoked significantly higher theta power in dlPFC and PCC (a physiologic signal biomarker). The abbreviations used in FIG. 8B can be defined as follows: dlPFC, dorsolateral PFC; dmPFC, dorsomedial PFC; vlPFC, ventrolateral PFC; dACC, dorsal anterior cingulate cortex; PCC, posterial cingulate cortex. FIG. 8C illustrates reaction time during open loop stimulation during MSIT. Markers represent individual participants, bars show the mean, and error bars show standard error of the mean. Stimulation improved flexibility of the subject resulting in improved task performance, as reflected in lower reaction times. The blocks are labeled to correspond to the stimulation sites in FIG. 7C, and inferential testing is performed against the unstimulated condition. FIG. 8D illustrates example theta power traces from PFC channels in two participants, with ventral (top) and dorsal (bottom) capsular stimulation. NS1 and NS2 trials are as in FIG. 7D. The stimulation was from 0-0.6 seconds (grey window). FIG. 8D illustrates task-evoked theta power (log ratio vs. pre-trial baseline), across PFC channels, in NS1 trials (None) compared to NS2 trials (all other conditions). Stimulation increased theta power, as in prior reports. In all panels, *, , and * denote $p<0.05$, 0.02, and 0.001 respectively, after appropriate correction.

Figure 8A:
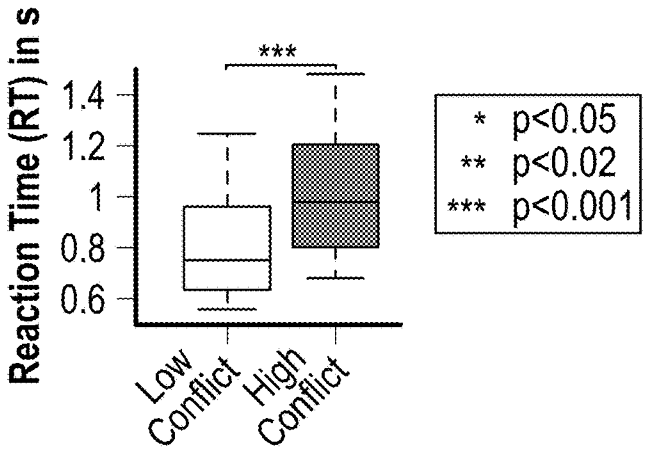
FIG. 8A is a graphical illustration of a bar chart depicting reaction time during unstimulated trials.
Figure 8B:
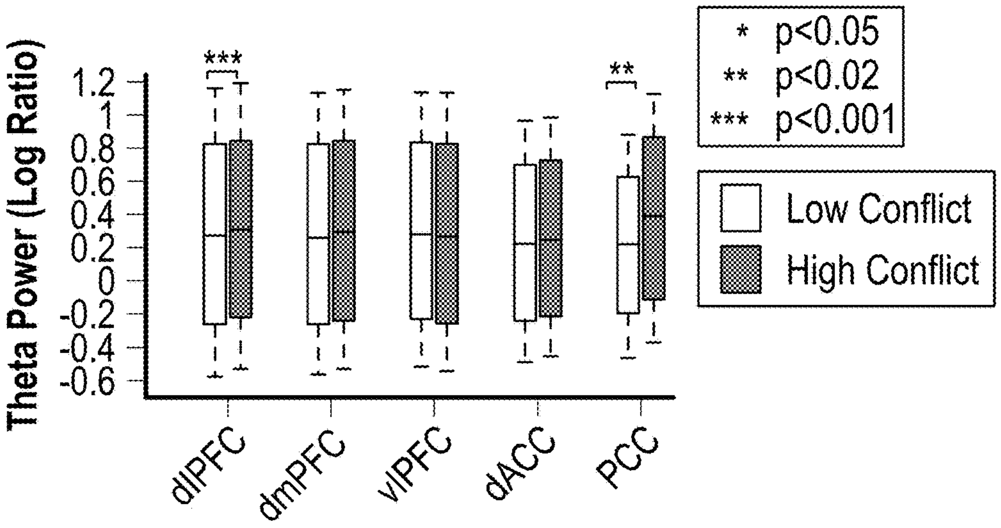
FIG. 8B is a graphical illustration of a bar chart depicting theta power ratio.
Figure 8C:
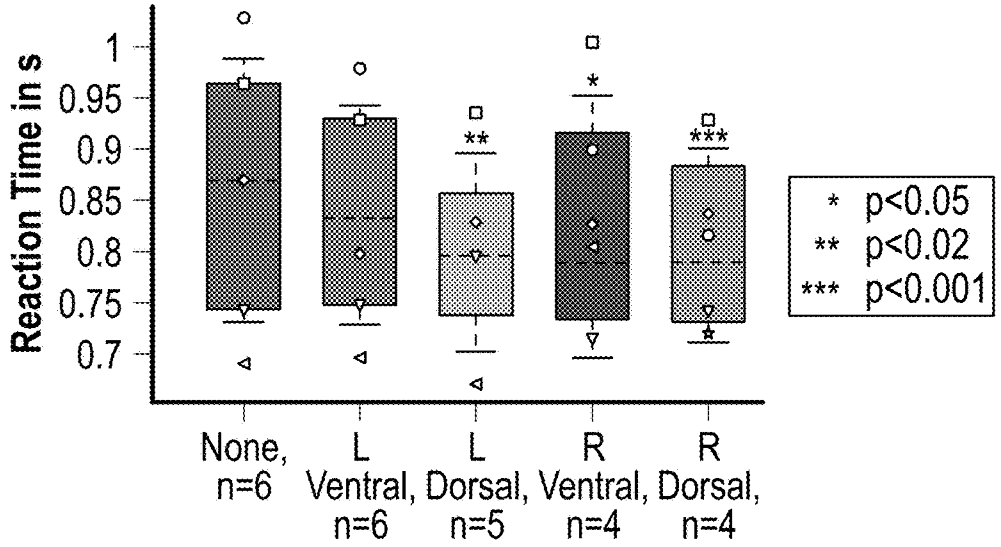
FIG. 8C is a graphical illustration of a bar chart depicting reaction time during open-loop stimulation.
Figure 8D:
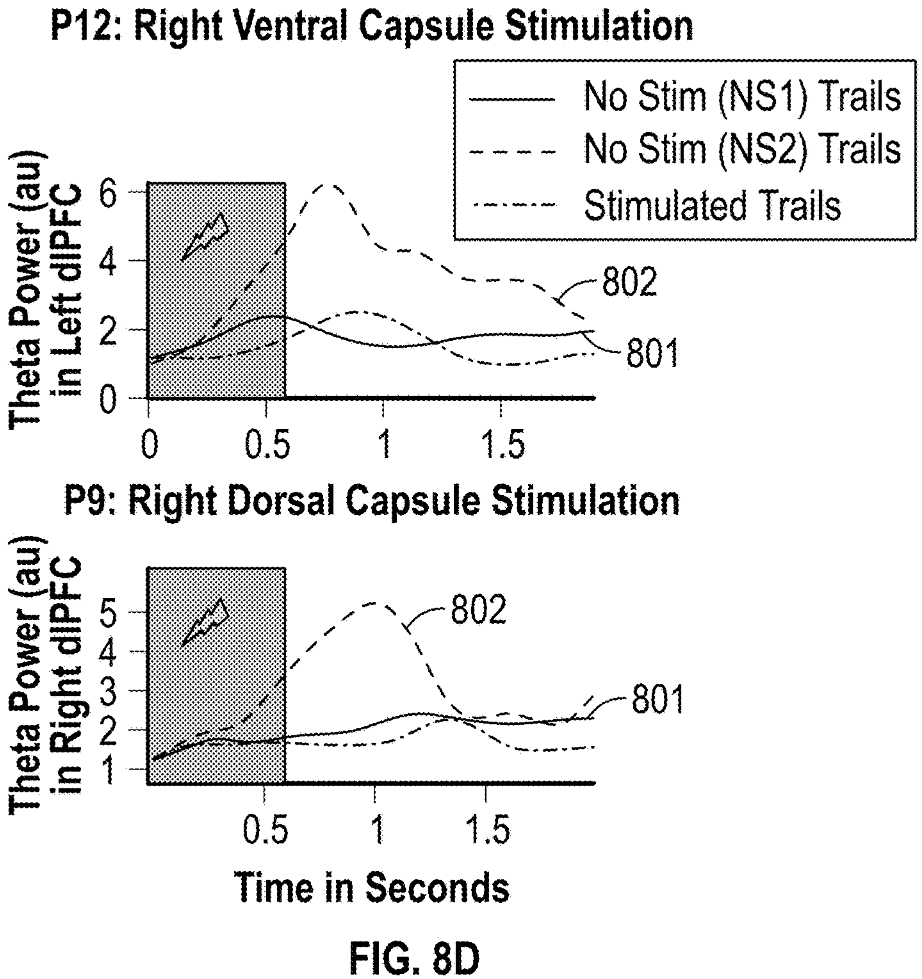
FIG. 8D is a graphical illustration of theta power traces.
Figure 8E:
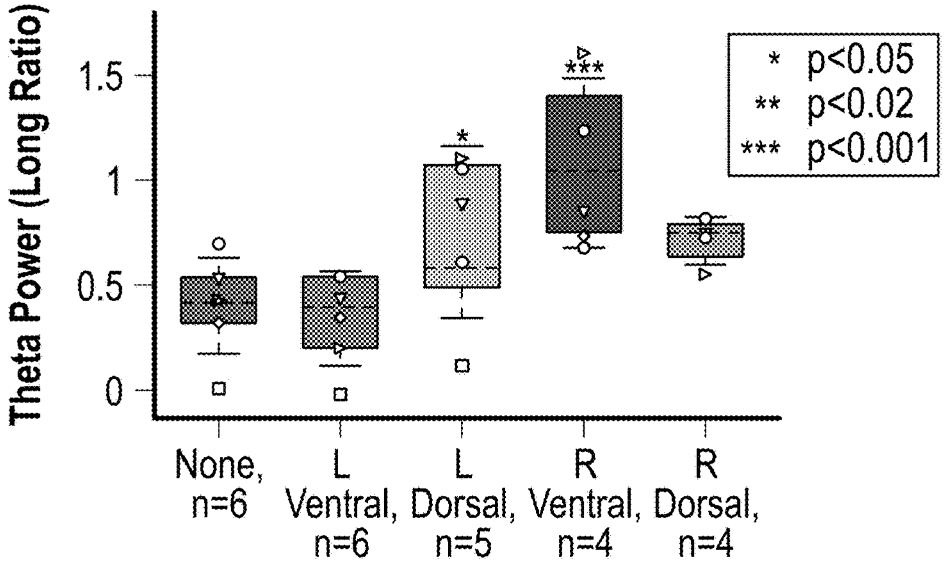
FIG. 8E is a graphical illustration of a bar chart depicting task-evoked theta power.

As illustrated in FIG. 8A, MSIT successfully engaged cognitive control: participants were 216 ms slower on high-conflict trials ($N=21$, $p<0.001$, $t=33.62$, Wald test on GLM coefficient). Conflict increased task-related theta power in the posterior cingulate ($p<0.02$, 3.24) and dorsolateral prefrontal cortex ($p<0.001$, $t=4.31$) (FIG. 8B). Stimulation enhanced both cognitive control and its electrophysiologic correlates. Right dorsal ($p<0.001$, $t=-4.28$), left dorsal ($p<0.01$, $t=-2.65$) and right ventral ($p<0.05$, $t=-2.64$) capsular stimulation all significantly decreased reaction time (FIG. 8C) without impairing accuracy. Reaction times under dorsal stimulation were faster than with ventral stimulation on both sides, with right dorsal being the overall most effective. There was no evidence for an interaction between stimulation and conflict level (AIC: −449.27 for a model without an interaction term vs. −445.72 with interaction). To assess stimulation's effect on theta, artifact-free trials interleaved within stimulated blocks (NS2, FIG. 7D) were analyzed and compared to blocks without stimulation (NS1). Left dorsal and right ventral capsular stimulation significantly increased theta power in NS2 (curve 802) compared to NS1 trials (curve 801) (LD: p=0.0428, RV: p=0.0006, FDR corrected, FIG. 8D). Right dorsal capsular stimulation also increased theta but did not reach significance (p=0.1733, FDR corrected).

Figures 9A, 9B, 9C, 9D:
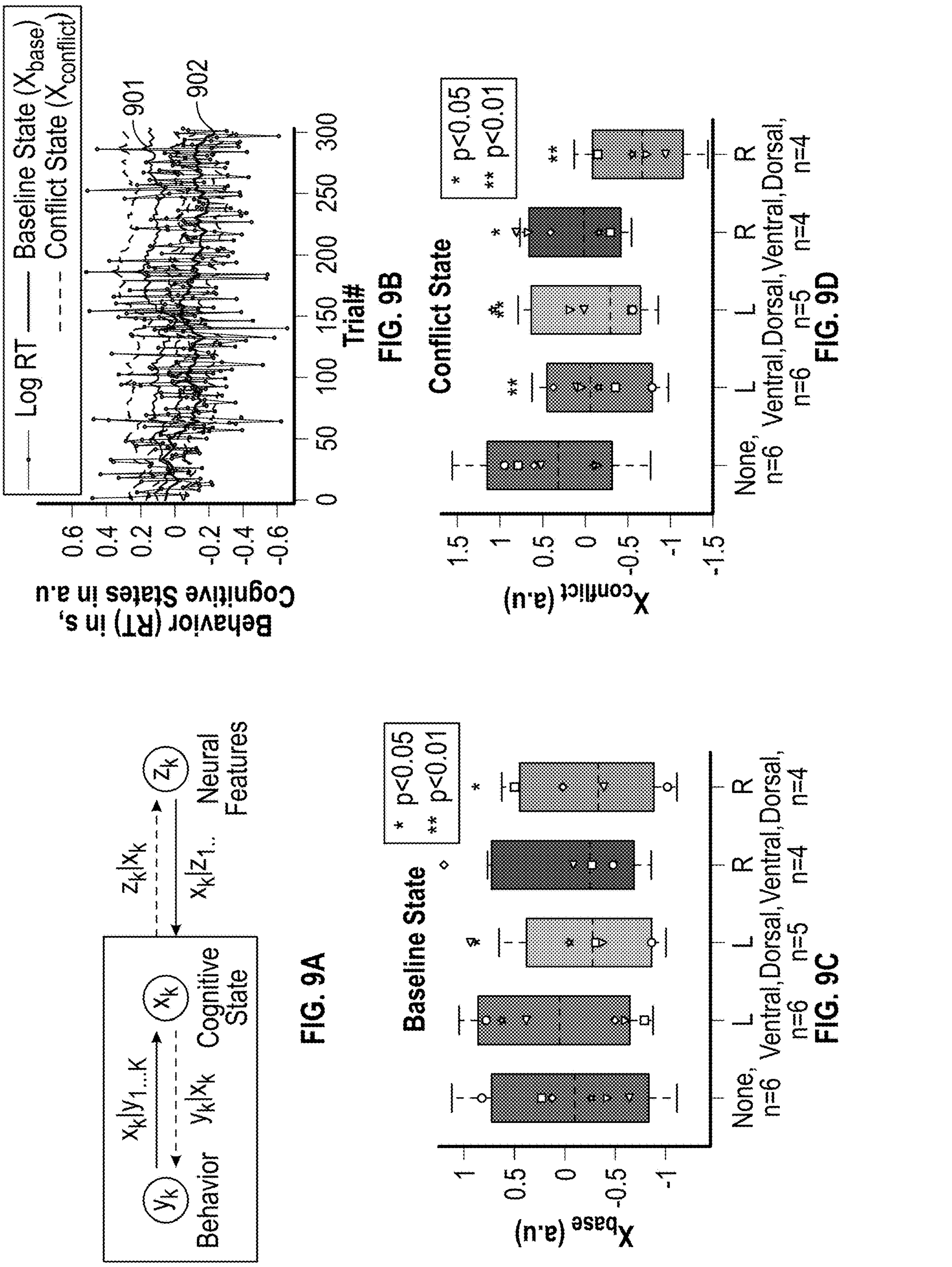
FIG. 9A is a schematic of modeling framework according to aspects of the present disclosure.
FIG. 9B is a graphical illustration of a subjects reaction time.
FIG. 9C is a graphical illustration of a bar chart depicting open-loop stimulation effects according to aspects of the present disclosure.
FIG. 9D is a graphical illustration of a bar chart depicting open-loop stimulation effects according to other aspects of the present disclosure.

As detailed below, open- and closed-loop stimulation based on a state-space model efficiently enhances cognitive control. FIG. 9 illustrates the effect of open-loop capsule stimulation on cognitive control. The stimulation's effects on cognitive control were quantified at a trial-to-trial level, using a state-space latent variable model (FIGS. 9A-B). This model separated changes in the baseline/expected reaction time ($x_{base}$) from immediate responses to high conflict ($x_{conflict}$). Stimulation in the dorsal capsule improved overall performance ($x_{base}$, FIG. 9C) and reduced conflict effects (FIG. 9D). Right dorsal capsular stimulation again had the largest effects. Ventral stimulation significantly reduced $x_{conflict}$, but not $x_{base}$.

FIG. 9A illustrates a schematic of the modeling framework, where behavior and neurophysiology are linked through a low-dimensional latent state space. Here, the focus was on inferring latent states from behavior (boxed). FIG. 9B illustrates an example of a participant's raw behavioral data (reaction time) and its decomposition into $x_{base}$ (curve 902) and $x_{conflict}$ (curve 901) to smooth out the raw behavioral data. As illustrated, responses to high conflict exhibited higher reaction times relative to baseline/expected performance. Further, $x_{base}$ and $x_{conflict}$ provide smoothed estimates of these reaction times and their changes, facilitating the discovery of correlative relationships. FIG. 9C illustrates an effect of open-loop, randomly interleaved stimulation on $x_{base}$ (expected reaction time). In this non-limiting example, dorsal stimulation improved this task component. FIG. 9D illustrates an effect of the same stimulation on $x_{conflict}$ (expected response to high conflict trials). Stimulation in all internal capsule sites altered this aspect of cognitive control, although right dorsal was still the most effective. Panels have the same formatting as FIG. 8. * and ** represent p<0.05 and p<0.01 respectively, again corrected for multiple comparisons between stimulation and baseline. Statistical inference is through non-parametric permutations due to the highly auto-correlated nature of the state variables.

FIG. 10 illustrates that closed-loop internal capsule stimulation efficiently enhances cognitive control relative to open-loop stimulation. Capsular stimulation under closed-loop control was applied in three further participants. $x_{base}$ was estimated in real time and triggered stimulation during control lapses, i.e. when $x_{base}$ increased beyond a predetermined threshold (FIG. 10A). Conditioning stimulation on $x_{base}$ specifically improved that variable (FIG. 10B) without enhancing $x_{conflict}$ (FIG. 10C). Closed-loop stimulation was more effective than open-loop. Stimulation of the right ventral capsule, which did not have significant effects in open-loop tests (FIG. 9C), now significantly reduced $x_{base}$ (p<0.01, permutation test, FIG. 10B). At both dorsal stimulation sites, closed-loop stimulation reduced $x_{base}$ significantly more than open-loop stimulation (p<0.001, permutation test, FIG. 10B). Closed-loop stimulation's effect was manifest in raw reaction time data for right dorsal capsule stimulation (p<0.001, permutation test). Closed-loop stimulation also appeared more efficient: it produced a greater change in $x_{base}$ per stimulation in the right capsule (FIG. 10D), although this did not reach the pre-determined significance threshold (RV: p=0.207, RD: p=0.293).

Figure 10B:
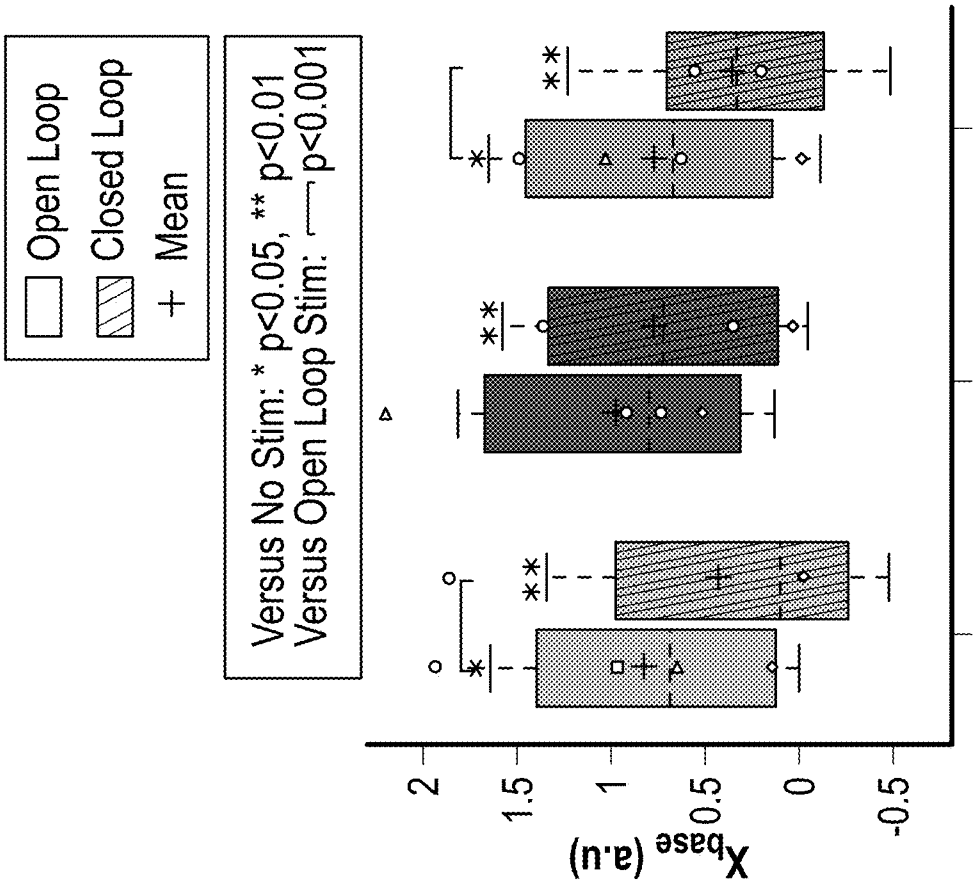
FIG. 10B is a graphical illustration of a bar chart open-loop vs. closed-loop stimulation effects according to aspects of the present disclosure.
Figure 10A:
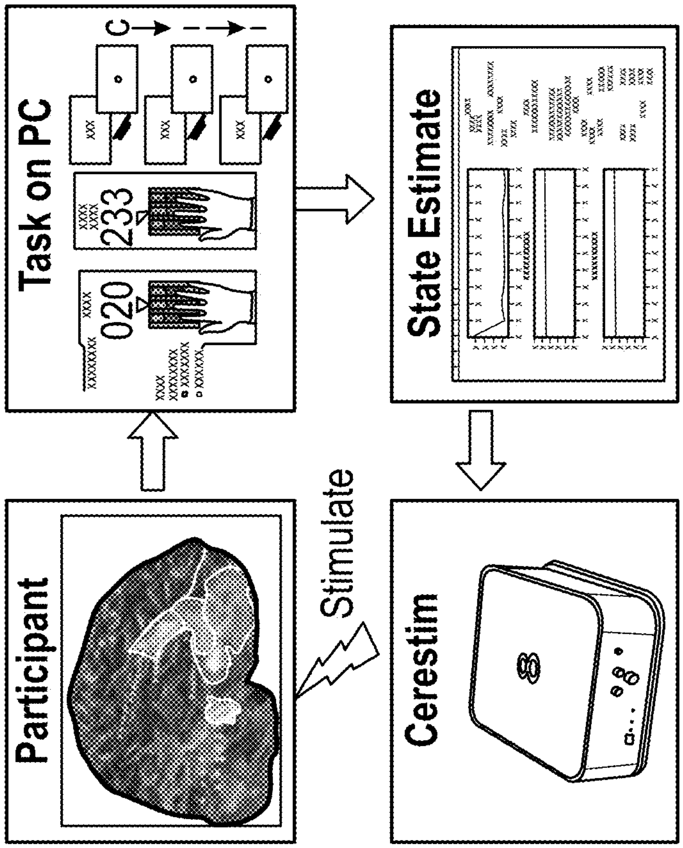
FIG. 10A is a schematic of a closed-loop stimulation paradigm according to other aspects of the present disclosure.
Figure 10C:
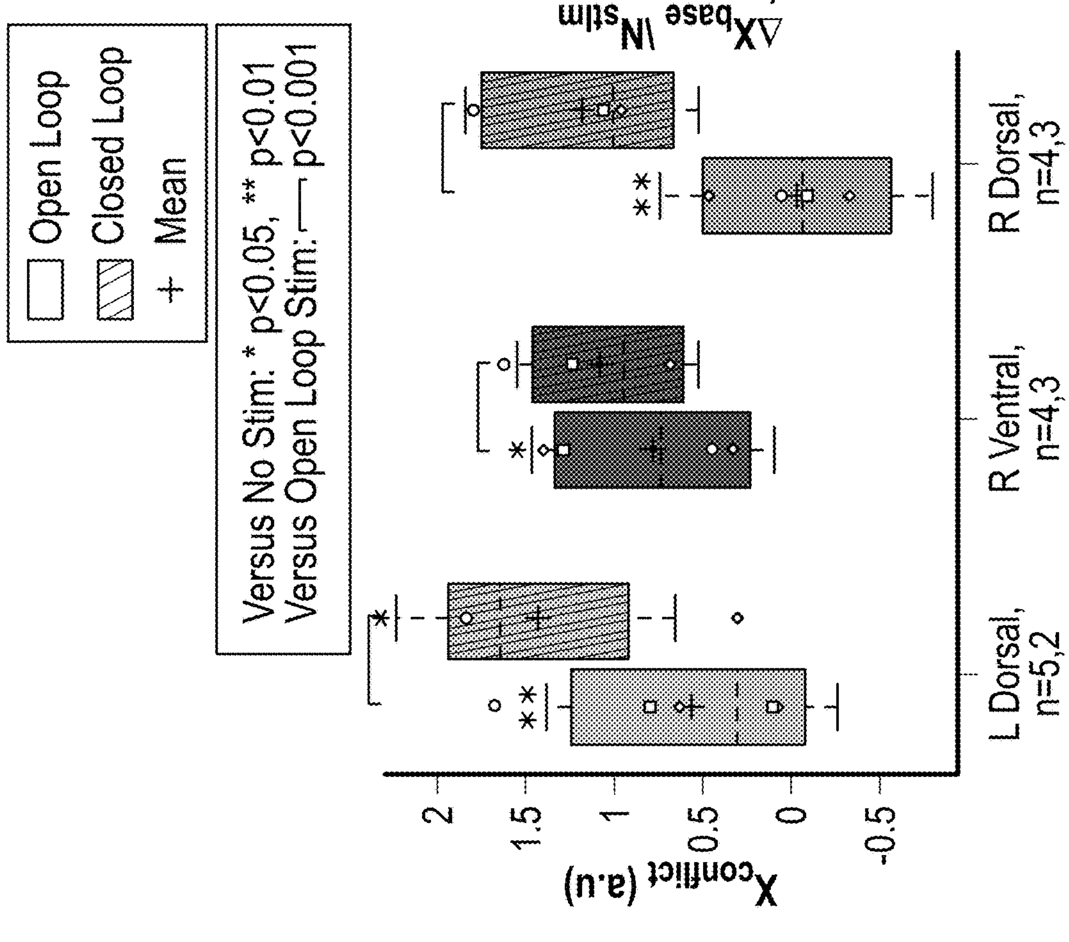
FIG. 10C is a graphical illustration of a bar chart open-loop vs. closed-loop stimulation effects according to other aspects of the present disclosure.
Figure 10D:
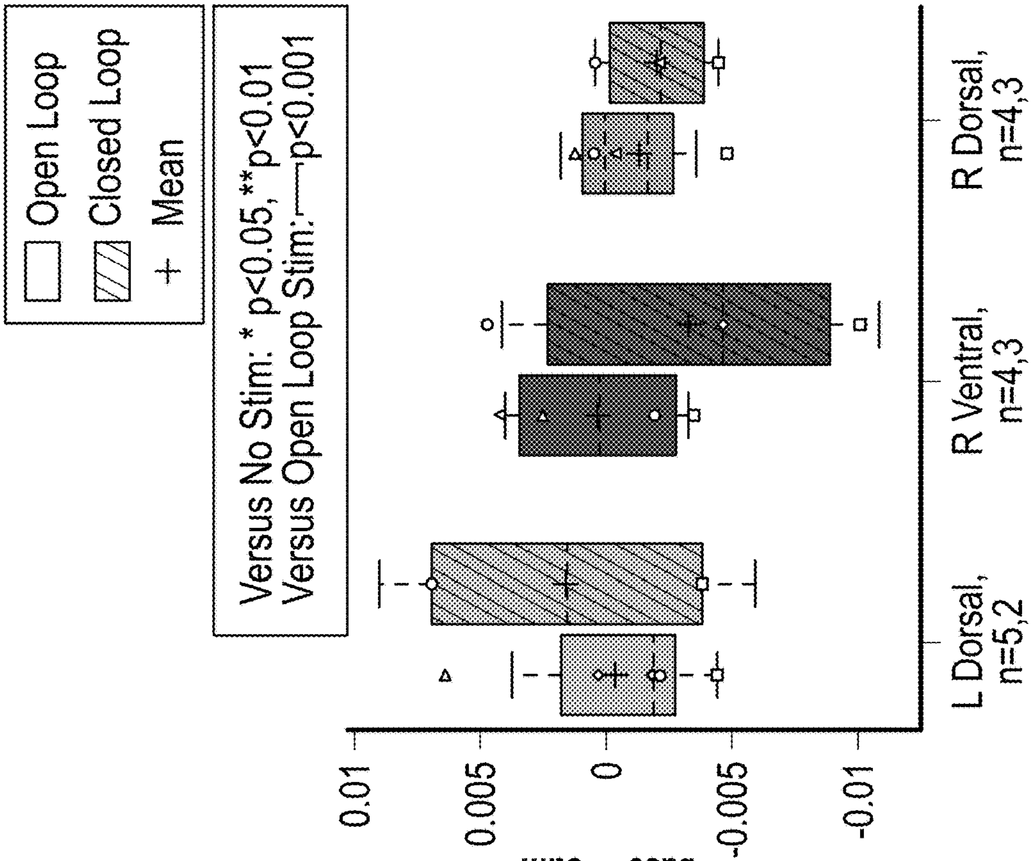
FIG. 10D is a graphical illustration of a bar chart open-loop vs. closed-loop stimulation effects according to other aspects of the present disclosure.

FIG. 10A illustrates a schematic of the closed loop paradigm. The controller estimates the baseline state after each trial (e.g., each iteration of the loop), commanding stimulation on the next trial if the state was above a pre-determined threshold. FIG. 10B illustrates an effect of open- vs. closed-loop stimulation on $x_{base}$. At multiple sites within the capsule, closed-loop stimulation was more effective at reducing $x_{base}$ (improving task performance). FIG. 10C illustrates an effect of open- vs. closed-loop stimulation on $x_{conflict}$. Stimulation conditioned on $x_{base}$ did not reduce $x_{conflict}$, and in fact significantly increased it at multiple sites. FIG. 10D illustrates an effect of open- vs. closed-loop stimulation on increase in mean $x_{base}$ ($\Delta X_{base}$) from unstimulated blocks (NS1) divided by the number of stimulated trials ($N_{stim}$). A negative value indicates a decrease (desired) in $x_{base}$ caused by a specific stimulation on a block level. FIGS. 10B-D follow the same formatting as prior Figures. State values in FIGS. 10B and C are normalized so that unstimulated blocks have a mean state value of 1 for each participant for both experiments, permitting comparison across participants. Significance in all panels is determined by a permutation test given the highly auto-correlated data. N for each experiment is given on the X-axis for open- and closed-loop participants.

FIG. 11 illustrates a method of identifying correlative relations ships by neural decoding of cognitive states using a state-space filtering model for closed-loop control. To demonstrate that cognitive control lapses could be remediated outside of a controlled, structured task setting, decoders were developed to read out cognitive control from LFP. For each participant, an encoding model (FIG. 11A) was estimated to map cognitive states to LFP power. State variables were linearly related to neural features (e.g., block 154 of FIG. 4). The confidence intervals of cognitive states decoded from LFP and estimated from behavior largely overlapped (FIG. 11B, $x_{base}$: 84.6±11% overlap, conflict: 80.6±16.2% overlap). Decoding used relatively few power features in each participant (FIG. 11C; 9.53±5.48 features for $x_{base}$ and 8.67±2.74 for $x_{conflict}$). Decoding weighted brain regions commonly implicated in cognitive control. $x_{base}$ was encoded primarily in dlPFC (4-55 Hz), vlPFC (65-110 Hz), accumbens (30-55 Hz), and temporal cortex (multiple bands). $x_{conflict}$ was more sparsely encoded in dlPFC (4-15 Hz), lateral OFC (8-15 Hz), and temporal cortex.

Decoding was also possible during intermittent brain stimulation ($x_{base}$: 86.3±6%, $x_{conflict}$: 82.2±18.9% of trials overlapping the confidence interval of the behavioral estimate). Stimulation marginally, but non-significantly, reduced the neural encoding of cognitive control. Both $x_{base}$ and $x_{conflict}$ required more neural features for decoding during stimulation (NS2) trials ($x_{base}$: 9.53±5.4 vs. 11.33±4.36 features; $x_{conflict}$: 8.67±2.74 vs. 10.22±4.06 features; all p>0.4, unpaired t-test). This was not caused by stimulation artifact, as we only decoded from NS2 trials. Stimulation also decreased the number of cortical regions that encoded either $x_{base}$ or $x_{conflict}$ (FIG. 11D). This encoding may have transferred to the dorsal striatum (caudate), which showed increased encoding across frequency bands, although this did not reach our pre-specified significance threshold for $x_{base}$ ($x_{base}$: t=−0.3980, p=0.6908, $x_{conflict}$: t=5.3947, p<0.001, paired t-test between NS1 and NS2 trials across participants).

Figure 11A:
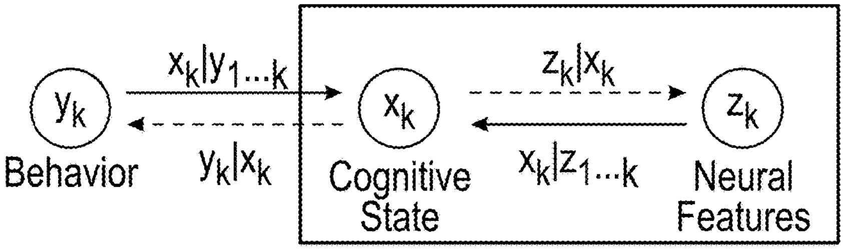
FIG. 11A is a schematic of an encoding-decoding framework according to aspects of the present disclosure.
Figure 11B:
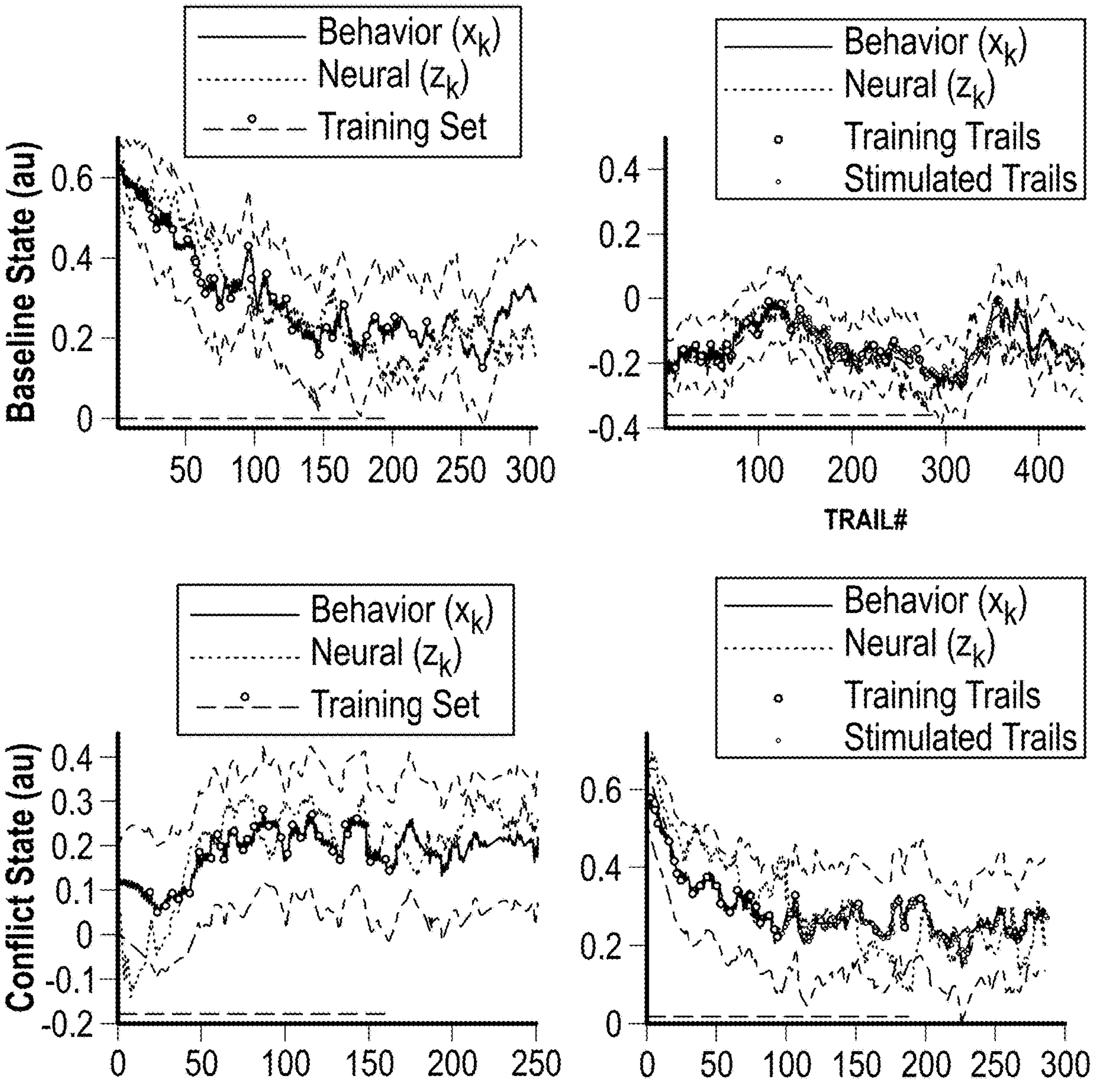
FIG. 11B is a graphical illustration depicting estimated cognitive states according to aspects of the present disclosure.
Figure 11C:
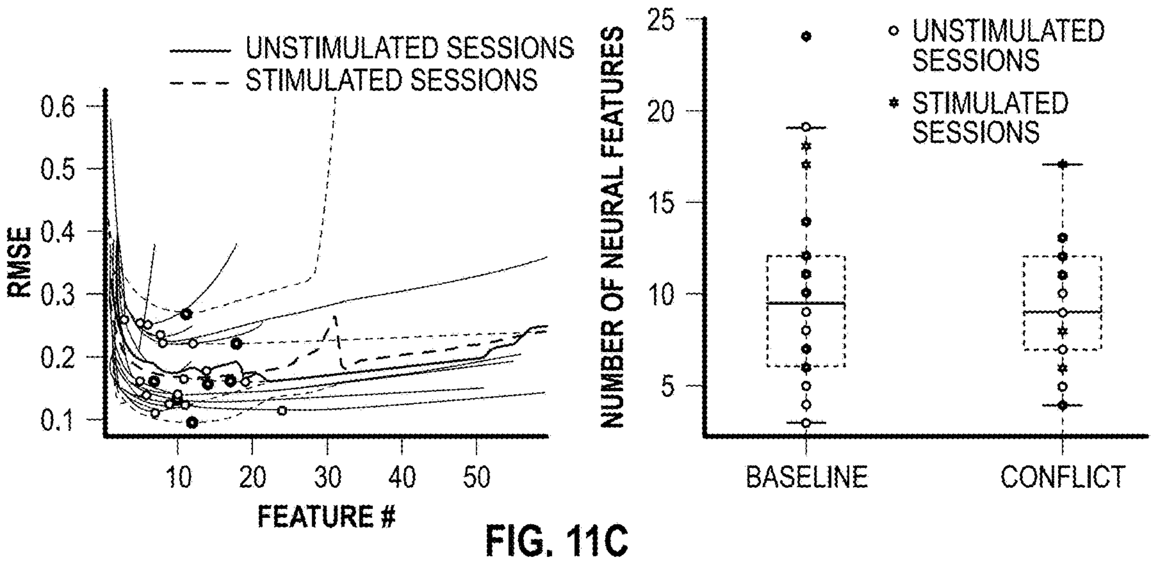
FIG. 11C is a graphical illustration depicting optimal neural features according to aspects of the present disclosure.
Figure 11D:
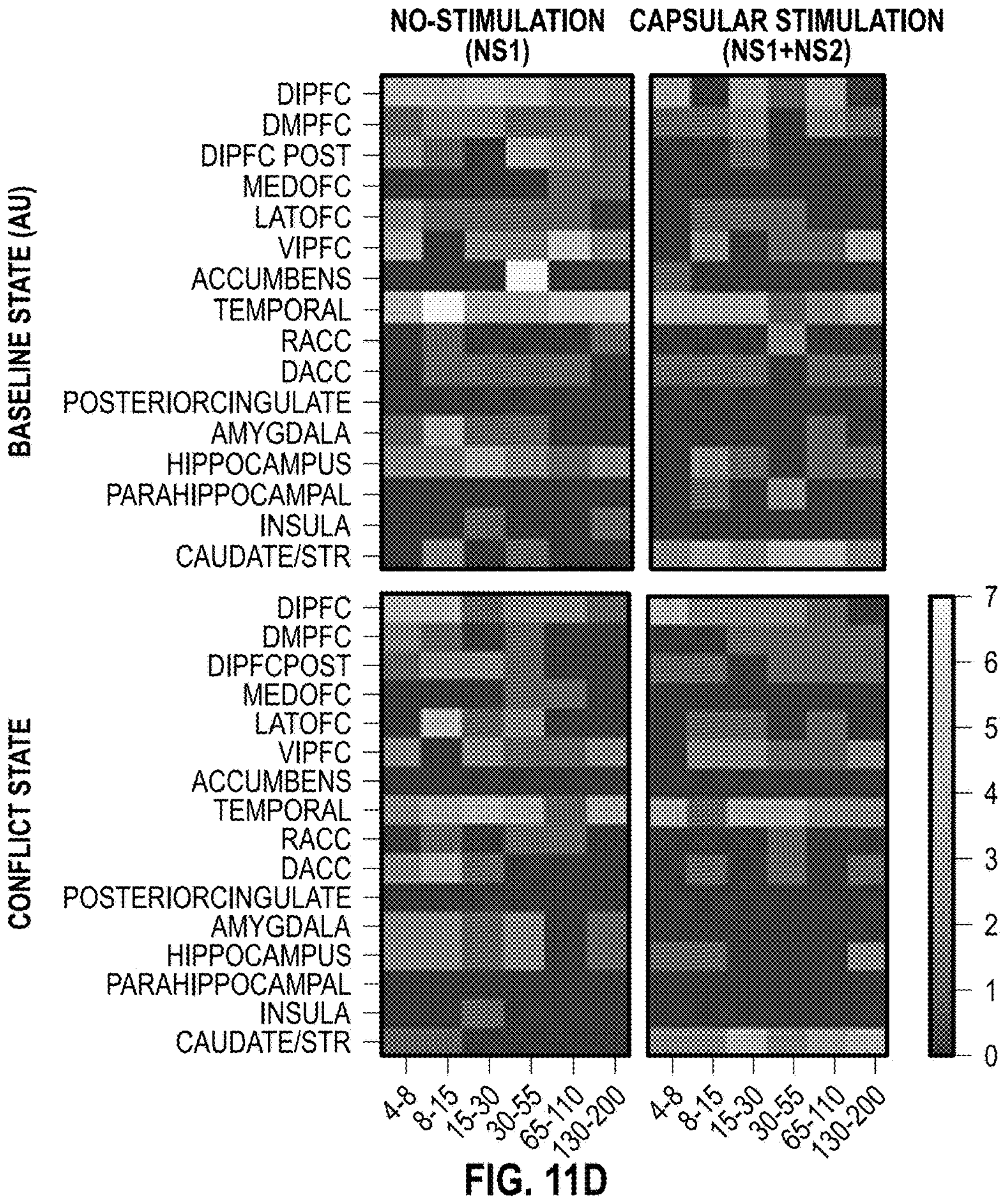
FIG. 11D is a graphical illustration of brain regions and frequency bands according to aspects of the present disclosure.

FIG. 11A illustrates a schematic of the encoding-decoding framework, which uses the same cognitive state variables as FIG. 9. Here, correlative relationships embodied in linear dependencies were identified between neural features of physiologic signals (e.g., LFP power) and the latent cognitive states (boxed within FIG. 11A). FIG. 11B illustrates examples, in two participants, of cognitive states as estimated from behavioral signals and from neural decoding. There is strong agreement throughout the task run, including on data not used to train the decoding model. Decoding quality is similar during unstimulated (left) and stimulated (right) experiments. FIG. 11C illustrates optimum neural feature set determined using a feature dropping analysis (left) to reduce the available signals to a lower-dimensional set of features, which can minimize error. Thin lines represent individual participants, thick lines the mean. The solid circles indicate the number of features that minimizes root mean squared error (RMSE) for $x_{base}$, for each participant, on a held-out validation set. This number of features did not differ between $x_{base}$ and $x_{conflict}$, or between stimulated and unstimulated blocks (right). FIG. 11D illustrates the number of participants encoding $x_{base}$ (top) and $x_{conflict}$ (bottom) in different brain regions and frequency bands during non-stimulated (left, NS1) and intermittent capsular stimulation (right, NS1+NS2) blocks. Capsular stimulation shifts encoding from cortical regions to subcortical, particularly caudate.

Cognitive control, an aspect or component of flexibility, is impaired in numerous mental disorders. The methods described herein can augment human cognitive control by intermittent closed-loop stimulation of the internal capsule. The effects were detectable in both manifest data (raw reaction times) and derived variables. Further, components of cognitive control could be separated and altered. The baseline state was enhanced without driving the conflict state in the same direction, illustrating that these two processes could be targeted separately. Both states could be decoded with a mean of 10 LFP spectral features per participant, from a mean of 6 brain regions. This is well within the processing power of modern neural implants. Importantly, the decoder was based on trial-structured data, but it could be used in a non-structured setting. In addition, periods of effortful cognitive control can be detected directly from LFP without any external event marker, as was illustrated in FIG. 5.

As described above, $x_{base}$ was enhanced, which reflects overall attentional focus. $x_{conflict}$ corresponds to the more immediate effect of conflict and the difficulty of executing control. In a clinical setting, either might be disrupted, and closed-loop control may need to be applied to both simultaneously. Here, when $x_{base}$ was controlled, $x_{conflict}$ significantly increased. These two states are not inherently anti-correlated, because both were reduced by open-loop stimulation (contrast FIGS. 9C-D against FIGS. 10B-C).

By way of another example, the present approach can be utilized to decode flexibility in brain activity of rodent models. Using probes (e.g., high density silicon probes), units and LFP from multiple PFC and striatal structures were recorded as wild-type (WT) Long-Evans rats perform a probabilistic reversal task. In a neural decoding framework analogous to that just described and that which will be shown, the physiologic features that predict flexible behavior can be identified. As will be shown, flexibility can correlate with PFC-striatal theta coherence, with a lesser correlation to spike-field locking within PFC.

Figure 12A:
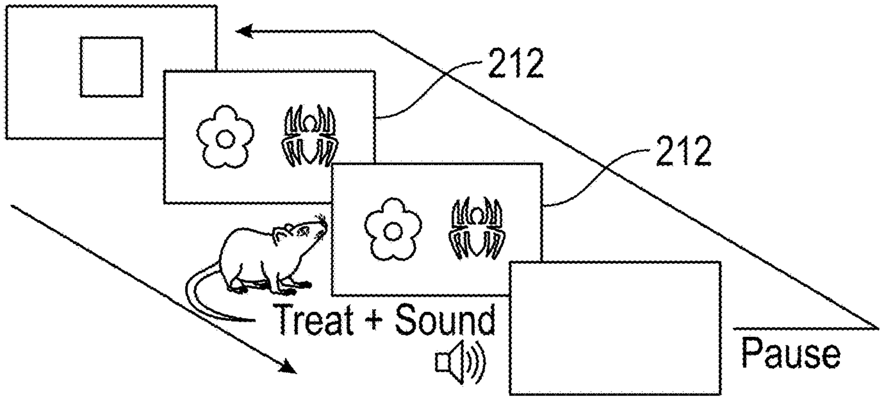
FIG. 12A is a schematic illustration of a task schema according to aspects of the present disclosure.

FIG. 12A illustrates a probabilistic reward learning (e.g., two-armed Bandit) task schema. Bandit tasks can reveal specific flexibility deficits in inflexibility disorders. Animals can be presented with highly distinguishable images 212 (e.g., a new pair each day), and select one by touching a touch-sensitive screen. In one non-limiting example, one image can be rewarded with a food pellet 80% of the time, the other 20% of the time. After a random number of correct (high-probability) responses, the contingencies switch, requiring the animal to flexibly update its contingency model to continue receiving rewards.

Figure 12B:
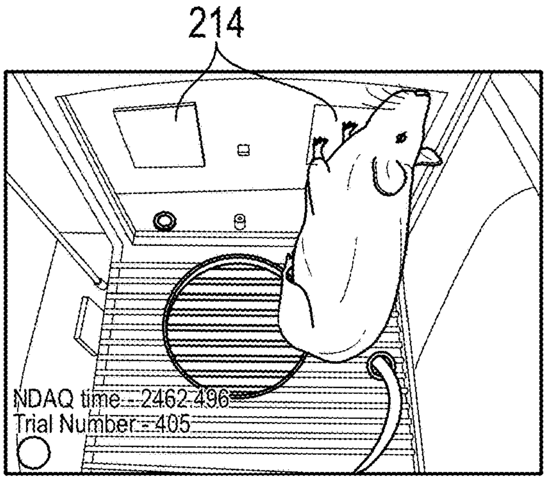
FIG. 12B is an illustration depicting a test apparatus according to aspects of the present disclosure.

FIG. 12B illustrates the wild-type Long-Evans rats performing the Bandit task in one non-limiting touchscreen-based example, wherein the rodent physically interacts with the touchscreen 214.

Figure 12C:
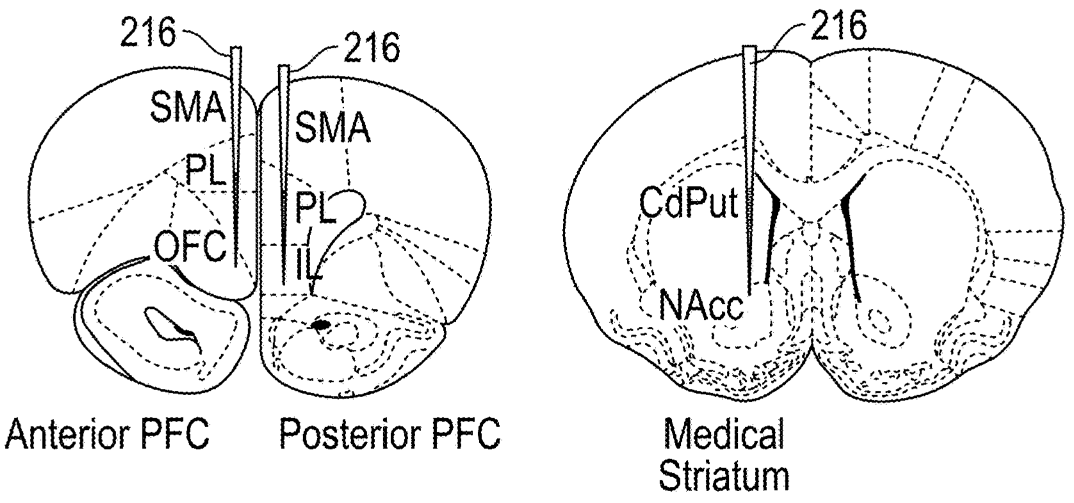
FIG. 12C is an exemplary illustration of a recording schema according to aspects of the present disclosure.

FIG. 12C illustrate an electrophysiologic data recording schema according to some embodiments. In one non-limiting example, animals can be implanted in PFC and striatum with probes 216 (e.g., high-density Neuropixel probes), which can chronically record hundreds of channels. The shank of these probes 216 may contain 960 recording sites, 348 of which may be active at any given time. Thus, this can permit high-density sampling of many neurons from multiple brain regions simultaneously, with electronic control over the active electrode set. Importantly, Neuropixels can be in communication with a recording system (e.g., see FIG. 2). In this way, two implants per rat can effectively capture the entire cortico-striatal circuitry (see FIG. 6C).

Analysis of the data may be conducted as follows. Single-unit waveforms from the Neuropixels can be sorted by the system depicted in FIG. 2. LFPs can then undergo wavelet decomposition after extracting the overall signal from each brain region (e.g. by singular value decomposition). From this, the system can then compute field-field coherence among instrumented regions and spike-field coupling within regions, both broken down to the canonical frequency bands (e.g., theta, alpha, beta, etc.). Coupling measures can be extracted at a single-trial level through a jackknife approach. All of these trial-level representations can then be collected in a neural decoding analysis to identify correlative relationships, where aspects of neural activity (spike rates, power, spike-field, field-field) can be identified as which best predict the extracted flexibility parameters. Then a statistically principled data reduction method for this type of feature selection can be conducted, overcoming multiple-comparison problems. To identify how these encoding relationships change within a trial, the process can be repeated at multiple time points with cluster-based significance correction. Flexibility (latent model variables) can be most strongly encoded in field-field theta coherence in the dorsal loops, i.e. from PL to dorsal striatum. Other variables, however, such as dorsal PFC ensemble spiking can also be selected by the decoding analysis, just in lower numbers or with weaker coefficients. As such, non-theta frequencies will not be selected. In other aspects, information flowing from ventral to dorsal PFC and thence to striatum can be observed. That is, in the sliding-window analysis, early time points can decode flexibility from ventral structures, with dorsal PFC and then striatal weighting in later time points.

In general, the systems and methods described herein enable real-time monitoring of human cognitive control, detection of lapses, and closed-loop remediation of those lapses. As appreciated from description above, herein provided systems and methods utilize a novel approach and have a broad range of applications, including for treatment of patients with various neurological and psychiatric disorders. Features suitable for such combinations and sub-combinations would be readily apparent to persons skilled in the art upon review of the present application as a whole.

The subject matter described herein and in the recited claims intends to cover and embrace all suitable changes in technology.

I claim:

1. A system for monitoring and controlling behavioral or cognitive flexibility of a subject, the system comprising:

a signal detection module for receiving physiologic signals from at least one source region of the subject's brain;

a signal generation module for generating at least one stimulation pulse; and a processor coupled to the signal detection module and signal generation module, the processor programmed to:

receive the physiologic signals from the at least one source region from the signal detection module;

receive behavioral signals from the subject;

determine at least one signal among the physiologic signals and the behavioral signals that is indicative of out-of-range behavioral flexibility using a coherence, a phase lag index, a cross-frequency coupling, a phase-amplitude coupling, an amplitude correlation, or a causality measure; and control the signal generation module to generate at least one stimulation pulse based on the at least one signal indicative of the out-of-range behavioral flexibility and deliver the at least one stimulation pulse to at least one target region.

2. The system of claim 1, wherein the at least one source region is within a cortico-striatal circuit.

3. The system of claim 2, wherein the at least one source region is within the lateral prefrontal cortex, medial prefrontal cortex, orbitofrontal cortex, amygdala, cingulate cortex, insula, hippocampus, dorsal medial striatum, ventral medial striatum, internal capsule, or basal ganglia.

4. The system of claim 2, wherein the at least one target region is within a cortico-striatal circuit.

5. The system of claim 4, wherein the at least one target region is within the lateral prefrontal cortex, medial prefrontal cortex, orbitofrontal cortex, amygdala, cingulate cortex, insula, hippocampus, dorsal medial striatum, ventral medial striatum, internal capsule, or basal ganglia.

6. The system of claim 2, wherein the physiologic signals include signals in at least one of the theta band or the alpha band.

7. The system of claim 1, wherein the behavioral signals correlate to the subject's performance of a task.

8. The system of claim 7, wherein the behavioral signals are based on the subject's response time during the performance of the task.

9. The system of claim 7, wherein the task is a Multi Source Interference Task (MSIT).

10. The system of claim 1, wherein the behavioral signals include a type of task the subject is performing.

11. The system of claim 10, wherein the type of task includes a Multi Source Interference Task (MSIT), Emotion Conflict Resolution (ECR) task, or reversal learning task.

12. A system for stimulation control for treating behavioral or cognitive flexibility of a subject, the system comprising:

a signal detection module for receiving signals from at least one source region of the subject's brain;

a signal generation module for generating at least one stimulation pulse; and a processor coupled to the signal detection module and signal generation module, the processor programmed to:

estimate model parameters based on behavioral and physiologic data;

implement a real-time engine that tracks a flexibility level of the subject using the model parameters as applied to the signals;

determine if the flexibility level is outside of a predetermined threshold range using a coherence, a phase lag index, a cross-frequency coupling, a phase-amplitude coupling, an amplitude correlation, or a causality measure; and upon the determination that the flexibility level is outside of the predetermined threshold range, cause the signal generation module to deliver a stimulation to at least one target region the subject's brain.

13. The system of claim 12, wherein the model parameters are estimated based on behavioral and physiological data acquired in the absence of brain stimulation.

14. The system of claim 12, wherein the flexibility level of the subject is at least partly based on the performance of the subject while performing a task.

15. The system of claim 14, wherein the flexibility level of the subject is at least partly based on the subject's response time during the performance of the task.

16. The system of claim 12, wherein the model parameters are estimated using a state-space filtering model, a regression model, or a classifier model.

17. The system of claim 12, wherein the at least one source region is within a cortico-striatal circuit.

18. The system of claim 17, wherein the at least one source region is within the lateral prefrontal cortex, medial prefrontal cortex, orbitofrontal cortex, amygdala, cingulate cortex, insula, hippocampus, dorsal medial striatum, ventral medial striatum, or basal ganglia.

19. The system of claim 17, wherein the at least one target region is within a cortico-striatal circuit.

20. The system of claim 19, wherein the at least one target region is within the lateral prefrontal cortex, medial prefrontal cortex, orbitofrontal cortex, amygdala, cingulate cortex, insula, hippocampus, dorsal medial striatum, ventral medial striatum, internal capsule, or basal ganglia.

21. A system for monitoring and controlling behavioral or cognitive flexibility of a subject, the system comprising:

a signal detection module for receiving physiologic signals from at least one source region of the subject's brain;

a signal generation module for generating at least one stimulation pulse; and a processor coupled to the signal detection module and signal generation module, the processor programmed to:

receive the physiologic signals from the at least one source region from the signal detection module;

receive behavioral signals from the subject;

determine at least one signal among the physiologic signals and the behavioral signals that is indicative of out-of-range behavioral flexibility, wherein the out-of-range flexibility is defined by a threshold defined by a signal-to-noise ratio of the behavioral signals, estimations of ranges of the behavioral signals, a relative change of the behavioral signals, a clinician-defined range of the behavioral signals, the at least one stimulation pulse, or an energy budget of an energy source of the system; and control the signal generation module to generate at least one stimulation pulse based on the at least one signal indicative of the out-of-range behavioral flexibility and deliver the at least one stimulation pulse to at least one target region.

22. A system for stimulation control for treating behavioral or cognitive flexibility of a subject, the system comprising:

a signal detection module for receiving signals from at least one source region of the subject's brain;

a signal generation module for generating at least one stimulation pulse; and a processor coupled to the signal detection module and signal generation module, the processor programmed to:

estimate model parameters based on behavioral and physiologic data;

implement a real-time engine that tracks a flexibility level of the subject using the model parameters as applied to the signals;

determine if the flexibility level is outside of a predetermined threshold range, wherein the threshold range is defined by a signal-to-noise ratio of the behavioral signals, estimations of ranges of the behavioral signals, a relative change of the behavioral signals, a clinician-defined range of the behavioral signals, the at least one stimulation pulse, or an energy budget of an energy source of the system; and upon the determination that the flexibility level is outside of the predetermined threshold range, cause the signal generation module to deliver a stimulation to at least one target region the subject's brain.

* * * * *